US008691228B2

(12) United States Patent
Ewert et al.

(10) Patent No.: US 8,691,228 B2
(45) Date of Patent: Apr. 8, 2014

(54) STABLE AND SOLUBLE ANTIBODIES INHIBITING TNFα

(71) Applicant: ESBATech, an Alcon Biomedical Research Unit LLC, Zurich-Schlieren (CH)

(72) Inventors: Stefan Ewert, Allschwil (CH); Alcide Barberis, Uitikon (CH); David Urech, Mannedorf (CH); Adrian Auf Der Maur, Rutihof (CH); Peter Lichtlen, Adliswil (CH)

(73) Assignee: ESBATech, an Alcon Biomedical Research Unit LLC (CH)

( * ) Notice: Subject to any disclaimer, the term of this patent is extended or adjusted under 35 U.S.C. 154(b) by 0 days.

(21) Appl. No.: 13/708,500

(22) Filed: Dec. 7, 2012

(65) Prior Publication Data

US 2013/0171143 A1 Jul. 4, 2013

Related U.S. Application Data

(60) Division of application No. 13/245,420, filed on Sep. 26, 2011, now Pat. No. 8,389,693, which is a continuation of application No. 11/916,793, filed as application No. PCT/CH2006/000300 on Jun. 6, 2006, now Pat. No. 8,067,547.

(60) Provisional application No. 60/785,353, filed on Mar. 23, 2006, provisional application No. 60/687,971, filed on Jun. 7, 2005.

(51) Int. Cl.
*A61K 39/00* (2006.01)

(52) U.S. Cl.
USPC ........................................ 424/133.1

(58) Field of Classification Search
None
See application file for complete search history.

(56) References Cited

U.S. PATENT DOCUMENTS

| | | | |
|---|---|---|---|
| 5,225,539 | A | 7/1993 | Winter |
| 5,644,034 | A | 7/1997 | Rathjen et al. |
| 5,654,407 | A | 8/1997 | Boyle et al. |
| 5,693,761 | A | 12/1997 | Queen et al. |
| 5,693,762 | A | 12/1997 | Queen et al. |
| 5,795,967 | A | 8/1998 | Aggarwal et al. |
| 5,821,337 | A | 10/1998 | Carter et al. |
| 5,859,205 | A | 1/1999 | Adair et al. |
| 6,090,382 | A | 7/2000 | Salfeld et al. |
| 6,171,586 | B1 | 1/2001 | Lam et al. |
| 6,180,370 | B1 | 1/2001 | Queen et al. |
| 6,406,863 | B1 | 6/2002 | Zhu et al. |
| 6,407,213 | B1 | 6/2002 | Carter et al. |
| 6,509,015 | B1 | 1/2003 | Salfeld et al. |
| 6,548,640 | B1 | 4/2003 | Winter |
| 6,639,055 | B1 | 10/2003 | Carter et al. |
| 6,693,762 | B2 | 2/2004 | Liu et al. |
| 6,982,321 | B2 | 1/2006 | Winter |
| 7,517,963 | B2 | 4/2009 | Rathjen et al. |
| 8,067,547 | B2 | 11/2011 | Ewert et al. |

FOREIGN PATENT DOCUMENTS

| | | | |
|---|---|---|---|
| WO | 9211383 | A1 | 7/1992 |
| WO | 03097697 | A2 | 11/2003 |
| WO | 2006131013 | A2 | 12/2006 |

OTHER PUBLICATIONS

Aud Fer Maur et al.; "Anti-independent selection of intracellular stable antibody frameworks"; Methods; vol. 24; pp. 215-224 (Apr. 8, 2004).
Doring et al.; "Identification and characterization of a TNF Alpha antagonist derived from a monoclonal antibody"; Molecular Immunology; vol. 31; No. 14; pp. 1059-1067 (Mar. 23, 1994).
Ewert et al.; "Stability improvement of anti bodies for extracellular and intracellular applications: CDR grafing to stable frameworks and structure-based framework engineering"; Methods; vol. 34; pp. 184-199 (2004).
Takahashi et al; "Production of humanized fab fragment against human high affinity IgE receptor in pichia pastoris"; Biosci. Biotechncol. Biochem.; vol. 64; No. 10; pp. 2138-2144 (2000).
Chowdhury and Wu; "Tailor-made antibody therapeutics"; Methods; vol. 36; pp. 11-24 (2005).
Worn and Plulckthun; "Stability Engineering of Antibody Single-chain Fv Fragments"; J. Mol. Biol; vol. 305; pp. 989-1010 (2001).
Extended European Search Report corresponding to application No. 11002906.3 dated Oct. 31, 2011.
James D. Marks, et al.; "By-Passing Immunization: Building High Affinity Human Antibodies by Chain Shuffling"; BioTechnology; vol. 10; Jul. 1992; pp. 779-783.
Carlos F. Barbas III, et al.; "In vitro evolution of a neutralizing human antibody to human immunodeficiency virus type 1 to enhance affinity and broaden strain cross-reactivity"; Proc. Natl. Acad. Sci. USA.; Medical Sciences; vol. 91; Apr. 1994; pp. 3809-3813.
Robert Schier, et al.; "Identification of functional and structural amino-acid residues by parsimonious mutagenesis"; Elsevier Science B.V.; Mar. 1995; pp. 147-155.
Dale E. Yelton, et al.; "Affinity Maturation of the BR96 Anti-Carcinoma Antibody by Codon-Based Mutagenesis"; The Journal of Immunology; vol. 155; Aug. 1995; pp. 2-12.
Jeffrey R. Jackson, et al.; "In Vitro Antibody Maturation"; The Journal of Immunology; vol. 154; pp. 2-11.
Robert Hawkins, et al.; "Selection of Phage Antibodies by Binding Affinity"; MRC Laboratory of Molecular Biology and MRC Centre for Protein Engineering; Jan. 1992; pp. 889-896.

*Primary Examiner* — Brad Duffy

(57) ABSTRACT

The present invention relates to particularly stable and soluble scFv antibodies and Fab fragments specific for TNFα, which comprise specific light chain and heavy chain sequences that are optimized for stability, solubility, in vitro and in vivo binding of TNFα, and low immunogenicity. Said antibodies are designed for the diagnosis and/or treatment of TNFα-related disorders. The nucleic acids, vectors and host cells for expression of the recombinant antibodies of the invention, methods for isolating them and the use of said antibodies in medicine are also disclosed.

20 Claims, 12 Drawing Sheets

ScFv antibody

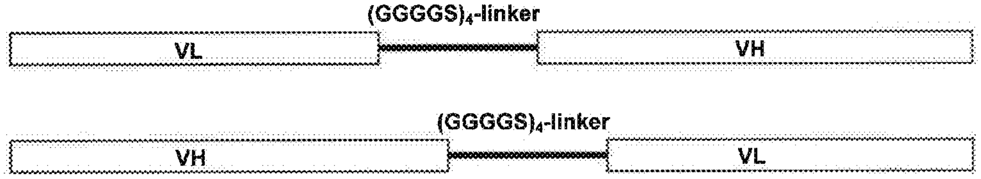

*VL*

```
TB-A     DIVMTQSPSS LSASVGDRVT LTCTASQSVS NDVVWYQQRP GKAPKLLIYS
TB-B     DIVLTQSPSS LSASVGDRVT LTCTASQSVS NDVVWYQQRP GKAPKRLIYS
             *                   R    GIR   ELA              *    A

TB-A     AFNRYTGVPS RFSGRGYGTD FTLTISSLQP EDVAVYYCQQ DYNSPRTFGQ
TB-B     AFNRYTGVPS RFSGSGSGTE FTLTISSLQP EDVAVYYCQQ DYNSPRTFGQ
         GSILQS          * *  *                *      Y SL YM

TB-A     GTKLEVKR
TB-B     GTKLEVKR
```

*VH*

```
TB-A     QVQLVQSGAE VKKPGASVKV SCTASGYTFT HYGMNWVRQA PGKGLEWMGW
TB-B     QVQLVQSGAE VKKPGASVKV SCTASGYSFT HYGMNWVRQA PGQGLEWMGW
                    *     *           *    G FLH          *       R

TB-A     INTYTGEPTY ADKFKDRFTF SLETSASTVY MELTSLTSDD TAVYYCARE-
TB-B     INTYTGEPTY ADKFKDRVTL TRDTSIGTVY MELTSLTSDD TAVYYCARE-
           PDS DTI    Q  QG * * ***  **                  *     VP

TB-A     RG------DA MDYWGQG TLVTVSS
TB-B     RG------DA MDYWGQG TLVTVSS
           TYLDPW Y F         *
```

FIG. 1

Production yield of scFv by expression in *E. coli*
A.
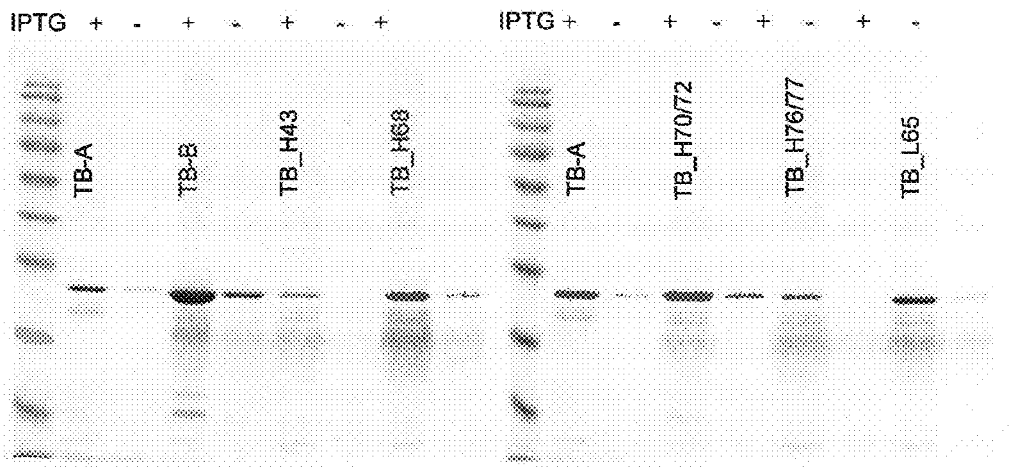
B.
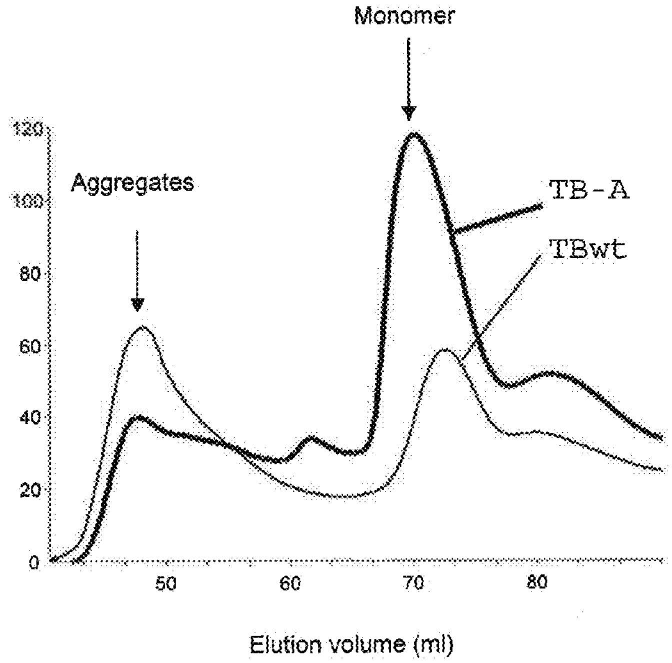
FIG. 3

Inhibition of TNF-induced cytotoxicity in L929 cells
A.
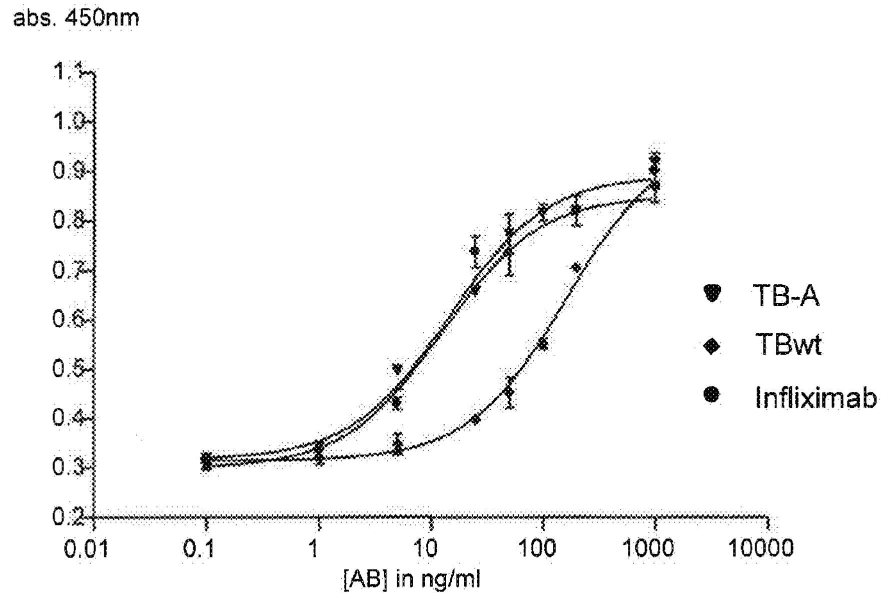
| | TB-A | TBwt | Infliximab |
|---|---|---|---|
| **$IC_{50}$ [ng/ml]** | 14.36 | 161.4 | 12.57 |
B.
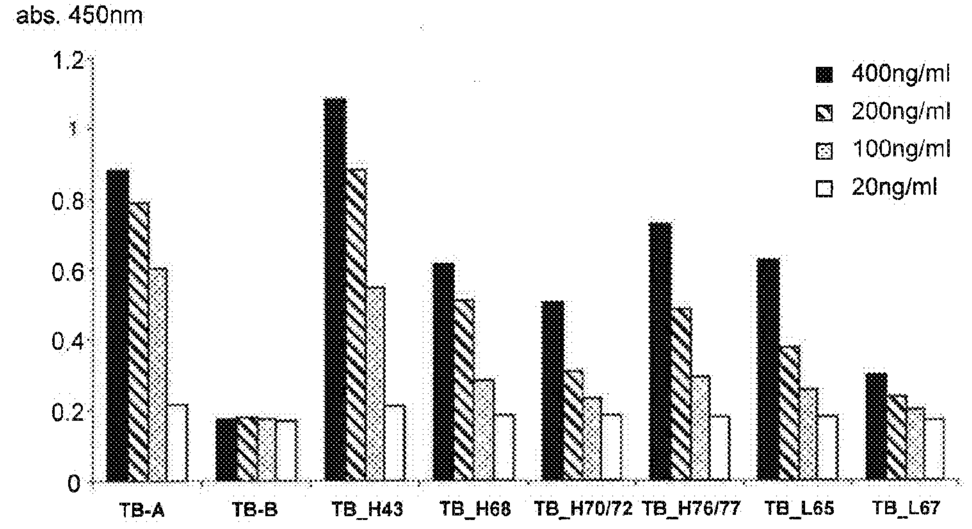
FIG. 5

C.

| | TB-A | TB-A Fab |
|---|---|---|
| $IC_{50}$ [ng/ml] | 29.7 | 65.9 |

| | serum | vitreous body fluid | TBSTM | urine | anterior chamber fluid |
|---|---|---|---|---|---|
| $K_d$ | 3.622 | 3.184 | 3.394 | 4.141 | 2.970 |

STABLE AND SOLUBLE ANTIBODIES INHIBITING TNFα

The present application is a divisional of U.S. application Ser. No. 13/245,420 filed Sep. 26, 2011 (now U.S. Pat. 8,389, 693); which is a continuation of U.S. application Ser. No. 11/916,793 filed May 27, 2008 (now U.S. Pat. No. 8,067, 547), which is the National Stage of International Application Ser. No.: PCT/CH2006/000300 filed Jun. 6, 2006, which claims benefit to U.S. Provisional patent application Ser. Nos. 60/785,353, filed Mar. 23, 2006, and 60/687,971 filed Jun. 7, 2005.

TECHNICAL FIELD

The present invention relates to optimised antibodies and antibody derivatives that bind to and block the function of tumour necrosis factor alpha (TNFα) and are useful for the diagnosis and/or treatment, prevention or amelioration of TNFα-associated diseases; their coding sequences, production, and use in pharmacologically suitable compositions.

BACKGROUND ART

Tumour necrosis factor alpha (TNFα, also known as cachectin), is a naturally occurring mammalian cytokine produced by numerous cell types, including monocytes and macrophages in response to endotoxin or other stimuli. TNFα is a major mediator of inflammatory, immunological, and pathophysiological reactions (Grell, M., et al. (1995) Cell, 83: 793-802).

Soluble TNFα is formed by the cleavage of a precursor transmembrane protein (Kriegler, et al. (1988) Cell 53: 45-53), and the secreted 17 kDa polypeptides assemble to soluble homotrimer complexes (Smith, et al. (1987), J. Biol. Chem. 262: 6951-6954; for reviews of TNF, see Butler, et al. (1986), Nature 320:584; Old (1986), Science 230: 630). These complexes then bind to receptors found on a variety of cells. Binding produces an array of pro-inflammatory effects, including (i) release of other pro-inflammatory cytokines such as interleukin (IL)-6, IL-8, and IL-1, (ii) release of matrix metalloproteinases and (iii) up regulation of the expression of endothelial adhesion molecules, further amplifying the inflammatory and immune cascade by attracting leukocytes into extravascular tissues.

A large number of disorders are associated with elevated levels of TNFα, many of them of significant medical importance. TNFα has been shown to be up-regulated in a number of human diseases, including chronic diseases such as rheumatoid arthritis (RA), inflammatory bowel disorders including Crohn's disease and ulcerative colitis, sepsis, congestive heart failure, asthma bronchiale and multiple sclerosis. Mice transgenic for human TNFα produce high levels of TNFα constitutively and develop a spontaneous, destructive polyarthritis resembling RA (Keffer et al. 1991, EMBO J., 10, 4025-4031). TNFα is therefore referred to as a pro-inflammatory cytokine.

TNFα is now well established as key in the pathogenesis of RA, which is a chronic, progressive and debilitating disease characterised by polyarticular joint inflammation and destruction, with systemic symptoms of fever and malaise and fatigue. RA also leads to chronic synovial inflammation, with frequent progression to articular cartilage and bone destruction. Increased levels of TNFα are found in both the synovial fluid and peripheral blood of patients suffering from RA. When TNFα blocking agents are administered to patients suffering from RA, they reduce inflammation, improve symptoms and retard joint damage (McKown et al. (1999), Arthritis Rheum. 42:1204-1208).

Physiologically, TNFα is also associated with protection from particular infections (Cerami. et al. (1988), Immunol. Today 9:28). TNFα is released by macrophages that have been activated by lipopolysaccharides of Gram-negative bacteria. As such, TNFα appears to be an endogenous mediator of central importance involved in the development and pathogenesis of endotoxic shock associated with bacterial sepsis (Michie, et al. (1989), Br. J. Surg. 76:670-671.; Debets. et al. (1989), Second Vienna Shock Forum, p. 463-466; Simpson, et al. (1989) Crit. Care Clin. 5: 27-47; Waage et al. (1987). Lancet 1: 355-357; Hammerle. et al. (1989) Second Vienna Shock Forum p. 715-718; Debets. et al. (1989), Crit. Care Med. 17:489-497; Calandra. et al. (1990), J. Infect. Dis. 161: 982-987; Revhaug et al. (1988), Arch. Surg. 123:162-170).

As with other organ systems, TNFα has also been shown to play a key role in the central nervous system, in particular in inflammatory and autoimmune disorders of the nervous system, including multiple sclerosis, Guillain-Barre syndrome and myasthenia gravis, and in degenerative disorders of the nervous system, including Alzheimer's disease, Parkinson's disease and Huntington's disease. TNFα is also involved in disorders of related systems of the retina and of muscle, including optic neuritis, macular degeneration, diabetic retinopathy, dermatomyositis, amyotrophic lateral sclerosis, and muscular dystrophy, as well as in injuries to the nervous system, including traumatic brain injury, acute spinal cord injury, and stroke.

Hepatitis is another TNFα-related inflammatory disorder which among other triggers can be caused by viral infections, including Epstein-Barr, cytomegalo-virus, and hepatitis A-E viruses. Hepatitis causes acute liver inflammation in the portal and lobular region, followed by fibrosis and tumor progression.

TNFα can mediate cachexia in cancer, which causes most cancer morbidity and mortality (Tisdale M. J. (2004), Langenbecks Arch Surg. 389:299-305).

The key role played by TNFα in inflammation, cellular immune responses and the pathology of many diseases has led to the search for antagonists of TNFα.

TNFα is an important cytokine whose systemic blockade carries the risk for increased frequency and severity of clinically manifested infections, in particular re-activation of latent tuberculosis and possibly other risks including induction of lymphomas, demyelinating diseases and heart failure.

One class of TNFα antagonists designed for the treatment of TNFα-mediated diseases are antibodies or antibody fragments that specifically bind TNFα and thereby block its function. The use of anti-TNFα antibodies has shown that a blockade of TNFα can reverse effects attributed to TNFα including decreases in IL-1, GM-CSF, IL-6, IL-8, adhesion molecules and tissue destruction (Feldmann et al. (1997), Adv. Immunol. 1997:283-350).

Antibodies directed against TNFα have been proposed for the prophylaxis and treatment of endotoxic shock (Beutler et al. (1985) Science: 234, 470-474). The use of anti-TNFα antibodies in the treatment of septic shock is discussed by Bodmer et al., 1993, (Critical Care Medicine, 21:441-446, 1993), Wherry et al., 1993, (Critical Care Medicine, 21:436-440) and Kirschenbaum et al., 1998, (Critical Care Medicine, 26:1625-1626).

A method for treating a neurodegenerative disease in a human by administering an anti-TNFα monoclonal antibody or a TNFα binding fragment thereof has been disclosed in US2003147891.

WO0149321 teaches the use of TNFα blockers including anti TNFα antibodies to treat neurologic and related disorders caused by TNFα. It provides a method for treating said disorders by administering a TNFα antagonist.

WO03047510 discloses various kinds of monoclonal and engineered antibodies directed against TNFα, their production, compounds comprising them and use in medicine.

Antibodies useful for therapies of TNFα mediated diseases are usually either monoclonal antibodies (mAB) produced by hybridoma technology from a natural source, usually a mouse, or engineered antibodies. The latter either correspond to naturally occurring antibodies in that they comprise full-length heavy and light chains, or to the Fab fragments that can also be generated from natural antibodies by proteolytic cleavage, or to single chain scFv antibodies wherein fragments of the variable heavy and light chain regions are linked by a peptide linker.

Both, heavy and light chains of an antibody comprise constant and variable domains. As non-human antibodies are immunogenic, the amount of human-like sequences in an antibody is often increased in a so-called "hybrid" antibody, which comprises constant regions of a human IgG, and variable regions matching the sequences of an animal antibody, in most cases murine antibodies with the desired specificity. These variable regions can then be further adapted to become more similar to a typical human antibody by mutagenesis, leading to a "humanised" antibody. In yet an alternative approach, only the antigen binding portions, i.e. the complementary determining regions (CDRs) of the variable regions of a mouse antibody are combined with a framework of a human antibody, resulting in a "CDR-grafted" antibody.

Monoclonal antibodies against TNFα have been described in the prior art. Meager et al., 1087 (Hybridoma 6:305-311) describe murine monoclonal antibodies against recombinant TNFα. Shimamoto et al., 1988, (Immunology Letters 17:311-318) describe the use of murine monoclonal antibodies against TNFα in preventing endotoxic shock in mice.

U.S. Pat. No. 5,919,452 discloses anti-TNFα chimeric antibodies and their use in treating pathologies associated with the presence of TNFα.

The use of anti-TNFα antibodies in the treatment of RA and Crohn's disease is discussed in Feldman et al. (1998), (Transplantation Proceedings 30:4126-4127), Adorini et al., 1997, (Trends in Immunology Today 18:209-211) and in Feldmann et al., 1997, (Advanced Immunology 64:283-350). The antibodies to TNFα used in such treatments are generally chimeric antibodies, such as those described in U.S. Pat. No. 5,919,452.

US20003187231 discloses humanised anti-TNFα antibodies with at least one non-human CDR region that have improved binding characteristics. Furthermore, in the International Patent Application WO 92/11383, recombinant antibodies, including CDR-grafted antibodies, specific for TNFα are disclosed. Rankin et al. (1995), (British J. Rheumatology 34:334-342) describe the use of such CDR-grafted antibodies in the treatment of RA.

WO9211383 discloses a recombinant, humanised CDR-grafted antibody specific for TNFα that is derived from the murine monoclonal antibody 61E7, hTNFI, hTNF3 or 101.4, and it teaches the production and use of said antibodies in diagnosis and/or therapy of TNFα-associated disorders.

Among the specific inhibitors of TNFα that have become commercially available only recently, a monoclonal, chimeric mouse-human antibody directed against TNFα (infliximab, Remicade™; Centocor Corporation/Johnson & Johnson) has demonstrated clinical efficacy in the treatment of RA (Elliott et al. 1994, Lancet 344:1105-1110; Mani et al. (1998), Arthritis & Rheumatism 41: 1552-1563). Infliximab has also demonstrated clinical efficacy in the treatment of the inflammatory bowel disorder Crohn's disease (Baert et al. 1999, Gastroenterology 116: 22-28.)

US22002037934 discloses the treatment of hepatitis by administration of an anti-TNFα antibody such as infliximab.

U.S. Pat. No. 6,428,787 teaches the treatment of neurologic and TNFα-associated diseases with anti-TNFα antibodies including infliximab, CDP571 and D2E7.

D2E7 (Adalimumab), a human anti-TNFα monoclonal antibody (Abbott) has been developed to treat RA and Crohn's disease (WO9729131). Celltech is developing CDP571 (EP0626389), a humanised monoclonal anti-TNFα IgG4 antibody to treat Crohn's disease and CDP870, a humanised monoclonal anti TNFα antibody fragment to treat RA. The local administration of said antibodies for treatment of localised disorders is disclosed in US2003185826.

Many single chain antibodies (scFvs) were generated against a multitude of different antigens, in particular because they can be easily selected for high binding capacity using techniques such as for example phage display or ribosome display. Moreover, scFv antibodies can be produced in microbial systems which are associated with fewer costs compared to the production of therapeutic full-length antibodies.

In addition to conventional extracellular and in vitro applications, scFvs have also been successfully used for intracellular applications (Worn et al. 2000, JBC, 28; 275(4):2795-2803; Auf der Maur et al. 2002, JBC, 22; 277(47):45075-45085; Stocks M R, 2004, Drug Discov Today. 15; 9(22):960-966); hence, scFvs directed against intracellular antigens have been developed. In general, intracellular expression of functional scFvs is limited by their instability, insolubility, and tendency to form aggregates. For this reason, in vivo screening systems for scFv antibodies, which are particularly soluble and stable under reducing conditions typical for the intracellular environment (e.g. nucleus, cytoplasm) have been successfully developed using a so called "Quality Control" screen (WO0148017; Auf der Maur et al. (2001), FEBS Lett. 508:407-412; Auf der Maur et al. (2004), Methods 34:215-224) and have led to the identification of particularly stable and soluble scFv framework sequences for such purposes (WO03097697). Furthermore, these frameworks show exceptional expression levels and enhanced stability and solubility properties also under natural, oxidizing conditions in the extracellular environment. Hence, these favourable biophysical and biochemical properties translate into favourable high production yields and enable these antibody fragments, once directed against specific antigens, to be applied locally and/or systemically as protein therapeutics in particular therapeutic areas. As both scFv antibodies and Fab fragments, in contrast to full-length antibodies, lack the Fc part that is recognized by the Fc-receptor of monocytes, such as e.g. natural killer cells, they do not evoke antibody-dependent cell-mediated cytotoxicity (ADCC) and thus do not provoke unspecific toxicity due to binding to Fc-receptors on non-target cells.

Hence, there is a need for new, effective forms of antibodies for the treatment for TNFα-associated disorders such as RA, particularly treatments that can provide sustained, controlled therapy by local administration with a low degree of side effects. The present invention provides antibodies, compositions and methods for effective and continuous treatment of inflammatory processes of arthritis and other TNFα-mediated disorders or pathophysiological mechanisms, in particular various forms of pain.

All publications and references cited herein are hereby incorporated by reference in their entirety.

DISCLOSURE OF THE INVENTION

Hence, it is a general object of the invention to provide a stable and soluble antibody or antibody derivative, which specifically binds TNFα in vitro and in vivo. In a preferred embodiment said antibody derivative is an scFv antibody or Fab fragment.

Now, in order to implement these and still further objects of the invention, which will become more readily apparent as the description proceeds, said antibody or antibody derivative is manifested by the features that it comprises a light chain variable domain being or derived from the sequence SEQ ID NO:1 that is combined with a heavy chain variable domain being or derived from the sequence SEQ ID NO:2, wherein in the case of a derived sequence said sequence has at maximum up to 5 changes within the framework of said VL domain and/or at maximum up to 9 changes within the framework of said VH domain.

A preferred embodiment of the present invention is said antibody or antibody derivative, wherein one or more amino acid changes are introduced at any of the positions in the framework, preferably at one or more positions selected from the group of the positions 4, 46, 65, 67 70, and 83 of the VL domain, and/or at one or more of the positions selected from the group of the positions 11, 16, 28, 43, 48, 68, 70, 71, 72, 73, 76, 77, 79, 93 and 112 of the VH domain. More preferably, at least one of the conversions leads to an amino acid present in SEQ ID NO:3 for VL and/or SEQ ID NO:4 for VH, and even more preferably at most 13 conversions in total are present.

Most preferably, said antibody or antibody derivatives comprises a VL domain of the sequence SEQ ID NO:1 and/or a VH domain of the sequence or derived from the sequence SEQ ID NO:2, or a VL domain of the sequence SEQ ID NO:11 and a VH domain of the sequence SEQ ID NO:4. If the VH domain of the antibody of the present invention comprises a VL domain of SEQ ID NO:1, in a preferred embodiment the VH sequence is derived from SEQ ID NO:2 such that the phenylalanine at position 68 is changed to either alanine, leucine, isoleucine or valine. Additional changes within VH are optional. scFv antibodies of this kind are given in SEQ ID NO:31, SEQ ID NO:33, SEQ ID NO:34, SEQ ID NO:35, SEQ ID NO:36, and SEQ ID NO:37.

In another preferred embodiment of the present invention said antibody or antibody derivative is derived from the antibody with the VL sequence SEQ ID NO:1 and the VH sequence SEQ ID NO:2 and comprises at least one amino acid residue that is converted in at least one of the CDRs to a residue present in the corresponding CDR of the VL sequence SEQ ID NO:5 and/or the VH sequence SEQ ID No:6 or SEQ ID NO:25.

In a much preferred embodiment of the present invention in said antibody or antibody derivative at least one of the CDRs of the group VL CDR2, VL CDR3, VH CDR2 or VH CDR3 is converted to the corresponding CDR of the VL sequence SEQ ID NO:5 and/or the VH sequence SEQ ID No:25 or SEQ ID NO:6.

Most preferably, said antibody or antibody derivative comprises the following VL/VH sequence combinations:

VL SEQ ID NO:7/VH SEQ ID NO:2,
VL SEQ ID NO:8/VH SEQ ID NO:2,
VL SEQ ID NO:1/VH SEQ ID NO:9,
VL SEQ ID NO:1/VH SEQ ID NO:25,
VL SEQ ID NO:1/VH SEQ ID NO:28,
VL SEQ ID NO:1/VH SEQ ID NO:29,
VL SEQ ID NO:26/VH SEQ ID NO:30,
VL SEQ ID NO:27/VH SEQ ID NO:30.

In another preferred embodiment the antibody or antibody derivative of the present invention has specificity to human TNFα. Preferably, antigen binding is characterized by a $K_d$ of ≈100 nM or less. More preferred is an antibody with a $K_d$ of 10 nM or less, and most preferred of 1 nM and less.

Antibody derivatives according to the present invention are for example Fc fusions, toxin fusions, fusions to enzymatic activities, different formats such as minibodies, diabodies, linear antibodies, single chain antibodies, bispecific antibody fragments, in particular scFv and Fab fragments.

Another preferred object of the present invention is a scFv antibody whose VL and VH domains are connected by a linker, preferably in a VL-linker-VH sequence arrangement. More preferably said linker has the sequence SEQ ID NO: 10.

Another preferred object of the present invention is a scFv antibody derived from SEQ ID NO:40 (TB-A). Such an antibody can be obtained by mutagenesis, and comprises three or less mutations in either framework, CDR and/or linker sequences. Preferably, the scFv antibody has the sequence SEQ ID NO: 20, SEQ ID NO: 21, SEQ ID NO: 22, SEQ ID NO: 23, SEQ ID NO: 24, SEQ ID NO:31, SEQ ID NO:32, SEQ ID NO:33, SEQ ID NO:34, SEQ ID NO:35, SEQ ID NO:36, SEQ ID NO:37, or SEQ ID NO:38.

Another preferred object of the present invention is the Fab fragment comprising a VL domain that is fused to the constant region of a human Ig kappa chain, and a VH domain that is fused to the CH1 domain of a human IgG, whereby the two fusion polypeptides are connected by an inter-chain disulfide bridge.

Still in another aspect the antibody or antibody derivative, e.g. the antibody fragment, of the present invention is labelled or chemically modified.

The present invention also provides a DNA sequence encoding any of the antibodies or antibody derivatives of the present invention, as well as a cloning or expression vector containing said DNA sequence. In addition, a suitable host cell transformed with said DNA sequence is provided, which preferentially is *E. coli*, a yeast or a mammalian cell.

Furthermore, a method for the production of the antibodies or antibody derivatives of the present invention is provided, comprising culturing of the host cell transformed with the DNA encoding any of said antibodies or antibody derivatives under conditions that allow the synthesis of said antibody or antibody derivative, and recovering said molecule from said culture. Preferably, said method provides an scFv antibody or Fab fragment purified from *E. coli*.

Another aspect of the present invention is the use of the antibodies or antibody derivatives provided by the present invention as a diagnostic tool for in vitro diagnostics, and/or as a pharmaceutical. This use is particularly preferred in the context of any TNFα related condition.

The present invention also encompasses a composition comprising an antibody or antibody derivative of the present invention in combination with a pharmaceutically acceptable carrier, diluent or excipient, said composition to be used as a medicament for the treatment of TNFα associated diseases.

In a further aspect the present invention provides a combination preparation comprising an antibody or antibody derivative of the present invention, preferably with a second compound that is not an antibody or antibody derivative specific for TNFα.

In yet another aspect of the present invention the vector comprising the DNA sequence encoding an scFv antibody of the present invention is used for gene therapy.

The treatment of TNFα associated diseases is achieved by blocking of TNFα due to a strong interaction of TNFα with the antibody or the antibody derivative. Preferably, a treatment of autoimmune, acute or chronic inflammation conditions, cancer-related diseases, pain, neurological and neurodegenerative disorders, infectious diseases and cardiovascular diseases is envisaged.

BRIEF DESCRIPTION OF THE DRAWINGS

The invention will be better understood and objects other than those set forth above will become apparent when consideration is given to the following de-tailed description thereof. Such description makes reference to the annexed drawings, wherein:

FIG. 1 shows a scheme of the scFv antibodies with the sequences of TB-A and TB-B delimiting the range of the most frequent variations. Asterisks designate positions at which amino acid changes in the framework of the antibodies of the present invention are tolerated. Amino acids indicated below the CDRs (the CDRs being emphasized with a gray background) can be used in the respective CDRs.

FIG. 3 shows the production yield of scFvs when expressed in *E. coli*. A. SDS-polyacrylamide gel electrophoresis of expressed proteins. B. Analytical gel filtration of TB-A and TB-wt showing superior solubility of TB-A.

MODES FOR CARRYING OUT THE INVENTION

It has been found that antibodies or antibody derivatives comprising the frameworks identified in the so called "quality control" screen (WO0148017) are characterised by a generally high stability and/or solubility and thus may also be useful in the context of extracellular applications such as neutralizing TNFα. The present invention provides antibodies or antibody derivatives characterized by enhanced stability and solubility that specifically recognize and bind TNFα and thus are suitable to block the function of TNFα in vivo. Said antibodies or antibody derivatives are characterized by a special framework derived from the "quality control" screen for antibodies with particularly stable and soluble frameworks independent of their antigen binding site that has been disclosed in EP1479694. If the frameworks used in the screening are human antibody frameworks, they can be considered as non-immunogenic frameworks for human applications. The CDRs of the antibodies of the present invention are identical to or derived from the CDRs of the murine monoclonal antibody Di62 (Döring et al., 1994) that specifically binds to human TNFα with a high affinity (Kd=0.4 nM) and can block TNFα binding to its receptor. In addition, Di62 inhibits human TNFα-induced cytotoxicity in mouse L929 cells. The obvious step of grafting the CDRs from the mouse antibody onto the apparently best suitable human acceptor framework with undefined antigen binding properties, said framework having the VL sequence SEQ ID NO:5 and the VH sequence SEQ ID NO:6, said sequences being linked by a $(GGGGS)_4$ linker (SEQ ID NO:10), resulted in an scFv antibody of the sequence

```
        (SEQ ID NO: 3 + SEQ ID NO: 10 + SEQ ID NO: 4)
DIVLTQSPSSLSASVGDRVTLTCTASQSVSNDVVWYQQRPGKAPKRLI

YSAFNRYTGVPSRFSGSGSGTEFTLTISSLQPEDVAVYYCQQDYNSPR

TFGQGTKLEVKRGGGGSGGGGSGGGGSGGGGSQVQLVQSGAEVKKPGA

SVKVSCTASGYSFTHYGMNWVRQAPGQGLEWMGWINTYTGEPTYADKF

KDRVTLTRDTSIGTVYMELTSLTSDDTAVYYCARERGDAMDYWGQGTL

Figure 4:
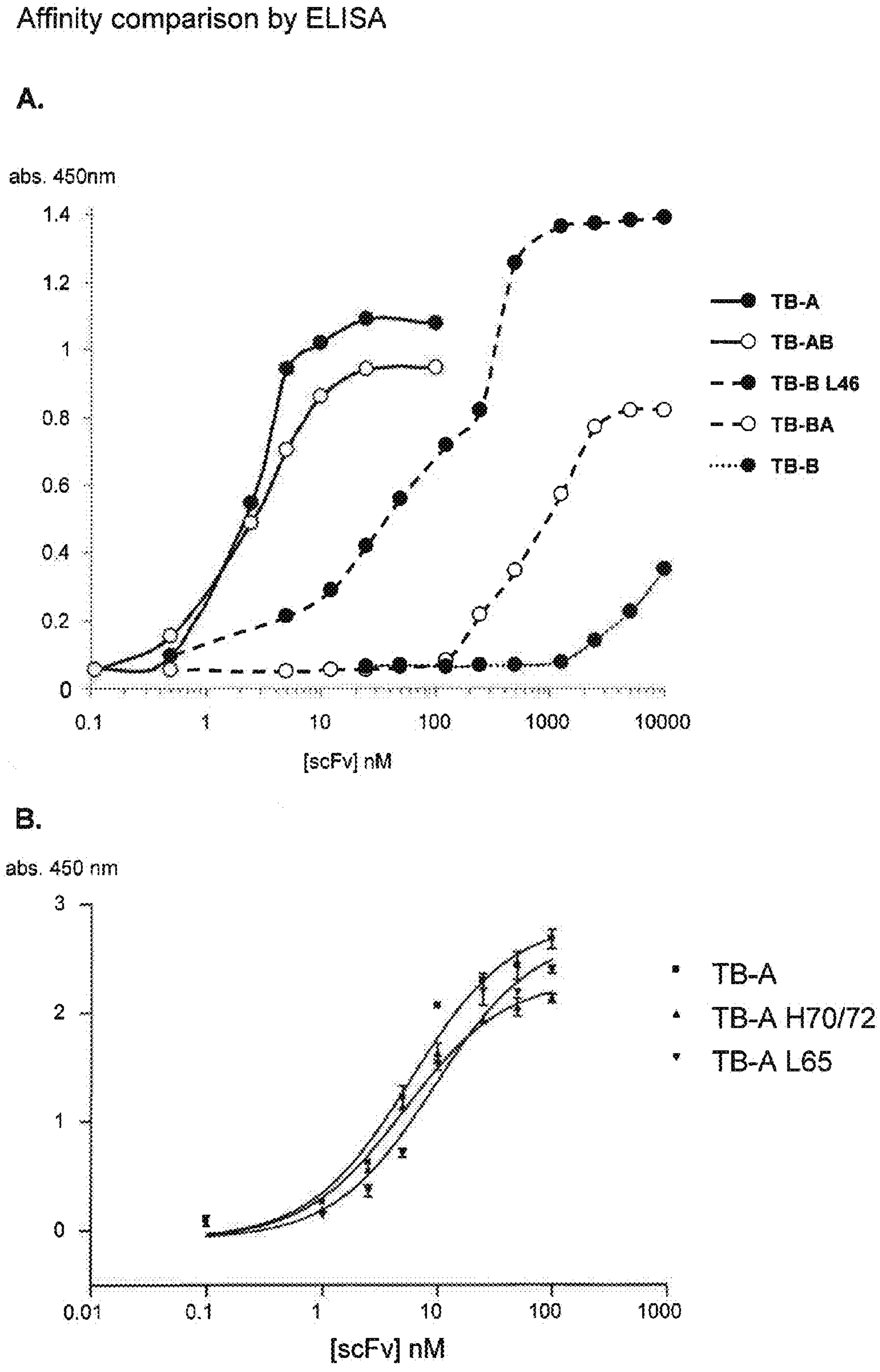
FIG. 4 shows a comparison of affinity of different scFv antibodies towards TNFα determined by ELISA.

VTVSS
``` said scFv antibody being called TB-B. TB-B gave good yields in protein expression (FIG. 3*a*), but was unable to specifically bind TNFα (FIG. 4*a*).

Hence, to obtain an antibody or antibody derivative that is (i) sufficiently specific for binding TNFα, (ii) sufficiently soluble to allow efficient production and purification and to block TNFα in vivo, (iii) sufficiently stable to be useful as a pharmaceutical without suffering a rapid degradation and (iv) sufficiently non-immunogenic, a compromise between best solubility and best antigen binding characteristics was sought by varying the framework and the CDRs. The present invention provides a sequence for VL and VH that is optimized for the combination of the criteria (i-iv). An scFv antibody comprising said VL (SEQ ID. NO:1 linked by a $(GGGGS)_4$ linker to said VH (SEQ ID NO:2) is called TB-A. The sequence of TB-A is given by SEQ ID NO:40. This antibody is still reasonably stable and soluble to give satisfactory yields when expressed and purified from *E. coli* (FIG. 3A), and it does not aggregate (FIG. 3B). Its binding characteristics towards TNFα are excellent, with a Kd of 0.8 nM.

The present invention also discloses VL and VH sequences derived from the sequences present in TB-A in various ways. First, point mutations at up to five positions in the framework of VL and/or at up to nine positions in the framework of VH have been found acceptable, especially point mutations that render the frameworks more TB-B-like, i.e. more like SEQ ID NO:3 for VL or SEQ ID NO:4 for VH. An scFv antibody comprising a VL domain of the sequence SEQ ID NO:11 and a VH domain of the sequence SEQ ID NO:4, linked by the $(GGGGS)_4$ linker, is called TB-B R46L because it differs only at position 46 of VL from TB-B. In contrast to TB-B this antibody still has good binding properties towards TNFα (Kd≈100 nM). This suggests that the number of changes in TB-B R46L relative to TB-A represents approximately the upper limit for changes in the variable domain framework.

In a preferred embodiment of the present invention only single or double point mutations are introduced into VL and/or VH frameworks of TB-A. The preferred framework residues for mutations are at positions 4, 46, 65, 67, 70 and 83 for VL, and at positions 11, 16, 28, 43, 48, 68, 70, 71, 72, 73, 76, 77, 79, 93 and 112 for VH. The positions are numbered according to the numbering in the sequence listings. The amino acids substitutions are preferably either "conservative", or such that the replacing amino acids are more similar or preferably even identical to the corresponding amino acids present in the TB-B sequence. For example, A76 of VH in TB-A can be changed to I76 as it is present in TB-B, but it may also be changed to another amino acid with similar, i.e. a non-polar side chain such as V or L. This is an example of a "conservative" amino acid substitution. Families of amino acid residues having similar side chains suitable for "conservative" substitutions as used herein have been defined in the art, including basic side chains (K, R, H), acidic side chains (D, E), uncharged polar side chains (Q, N, S, T, Y, C), non-polar side chains (G, A, V, L, I, P, F, M, W), beta-branched side chains (T, V, I) and aromatic side chains (Y, F, W, H). A preferred conservative change is that of VL at position 83, in that V is changed to either F (SEQ ID NO:26) or to A (SEQ ID NO: 27). However, in SEQ ID NO: 32 a non-conservative change in VL is V83E, which is combined with a change in CDR1, i.e. N31D, and in VH with V79A. Another extraordinary TB-A variant is that of SEQ ID NO: 33, with a conservative F68L exchange in VH connected to VL by a linker carrying an R at position 2, replacing G.

Much preferred single amino acid exchanges are R65S or Y67S in VL and K43Q or F68 to V, L, or A in VH. Much preferred double changes are F70L/L72R or A76I/S77G in VH. ScFv antibodies comprising TB-A sequences with said alterations show inhibition of TNFα induced cytotoxicity in L929 cells. The results of some of them are shown in FIG. 5B. Their sequences are as follows:

SEQ ID NO:18=TB-A H_K43Q (TB-A H43)
SEQ ID NO:19=TB-A H_F68V (TB-A H68)
SEQ ID NO:20=TB-A H_F70L/L72R (TB-A H70/72)
SEQ ID NO:21=TB-A H_A76I/S77G (TB-A H76/77)
SEQ ID NO:22=TB-A L_L46R (TB-A L46)
SEQ ID NO:23=TB-A L_R65S (TB-A L65)
SEQ ID NO:24=TB-A L_Y67S (TB-A L67)

In a preferred embodiment any of the above mentioned VH domains may be combined with any of the above mentioned VL domains.

In another preferred embodiment of the present invention the VL and VH domains of TB-A and TB-B are shuffled such that the VL domain of TB-A (SEQ ID. NO:1 is combined with the VH domain of TB-B (SEQ ID NO:4), or the VL domain of TB-B (SEQ ID. NO:4) is combined with the VH domain of TB-A (SEQ ID NO:2). In a much preferred embodiment the shuffled versions obtained in an scFv are connected with the $(GGGGS)_4$ linker of the sequence SEQ ID. NO:10, resulting in the scFv antibodies TB-AB (SEQ ID. NO:12) or TB-BA (SEQ ID. NO:13), respectively. Said $(GGGGS)_4$ linker can have an amino acid exchange of a glycine to a more hydrophilic, i.e. polar, or even charged amino acid, which may render the antibody more soluble. Among these variations, the one with the sequence GRGGS-(GGGGS)3 (SEQ ID NO:39) is preferred.

It is also within the scope of the present invention to combine VL or VH domains of TB-B-like sequences with VH or VL domains of TB-A-like sequences, whereby TB-B/TB-A-like means that the sequences are closer to the one than to the other.

In yet another preferred embodiment of the present invention one or more amino acids are changed in the CDR regions of the TB-A VL and/or VH sequences to match the corresponding amino acids present in the selected sequences SEQ ID NO:5 of VL and/or SEQ ID. NO:6 or SEQ ID NO:25 of VH. Much preferred are changes in one of the VL CDRs (VL CDR2 or VL CDR3) and/or VH CDRs (CDR2 or CDR3), with the most preferred changes leading to the VL sequences SEQ ID NO:7 or SEQ ID NO:8 and/or the VH sequences SEQ ID NO:25 or SEQ ID NO:9, respectively.

In another preferred embodiment of the present invention the VL sequences SEQ ID NO:26 or SEQ ID NO:27 is combined with the VH sequence SEQ ID NO:30. In yet another preferred embodiment of the present invention the VL sequence SEQ ID NO:1 is combined with the VH sequences Seq ID NO:28 or SEQ ID NO:29. Generally, any of the disclosed VL sequences may be combined with any of the disclosed VH sequences.

Objects of the present invention are antibodies and antibody fragments, in particular VL or VH polypeptides, single-chain antibodies (scFv) or Fab fragments. In the case of scFv antibodies, a selected VL domain can be linked to a selected VH domain in either orientation by a flexible linker. A suitable state of the art linker consists of repeated GGGGS amino acid sequences or variants thereof. In a preferred embodiment of the present invention a $(GGGGS)_4$ linker of the sequence ID NO:10 or its derivative SEQ ID NO: 39 is used, but variants of 1-3 repeats are also possible (Holliger et al. (1993), Proc. Natl. Acad. Sci. USA 90:6444-6448). Other linkers that can be used for the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol. Immunother. 50:51-59. The arrangement can be either VL-linker-VH or VH-linker-VL, with the former orientation being the preferred one.

Figure 2:
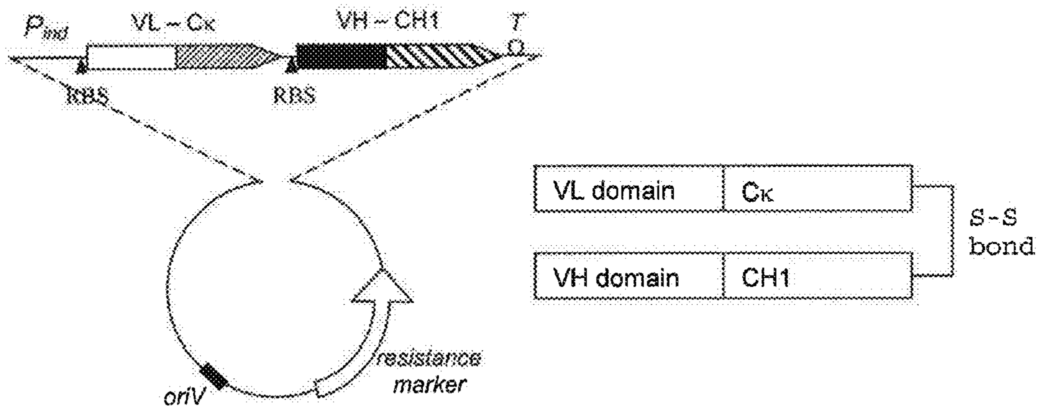
FIG. 2 shows an exemplary scheme for the expression of a Fab fragment.

In the case of Fab fragments, selected light chain variable domains VL are fused to the constant region of a human Ig kappa chain, while the suitable heavy chain variable domains VH are fused to the first (N-terminal) constant domain CH1 of a human IgG. In an exemplary embodiment of the present invention, the human Cκ domain has the sequence SEQ ID NO:14 and the CH1 domain used to construct the Fab fragments has the sequence SEQ ID NO:15. FIG. 2 shows an example of a Fab fragment wherein the VL and VH domains of TB-A are used such that the VL domain is directly linked to the human kappa constant domain, resulting in the sequence

```
                          (SEQ ID NO: 1 + SEQ ID NO: 14)
DIVMTQSPSSLSASVGDRVTLTCTASQSVSNDVVWYQQRPGKAPKLLI

YSAFNRYTGVPSRFSGRGYGTDFTLTISSLQPEDVAVYYCQQDYNSPR

TFGQGTKLEIKRTVAAPSVFIFPPSDEQLKSGTASVVCLLNNFYPREA

KVQWVDNALQSGNSQESVTEQDSKDSTYSLSSTLTLSKADYEKHKVYA

CEVTHQGLSSPVTKSFNRGEC
```

and the VH domain is fused to the first constant domain (CH1), resulting in the sequence

```
                          (SEQ ID NO: 2 + SEQ ID NO: 15)
QVQLVQSGAEVKKPGASVKVSCTASGYTFTHYGMNWVRQAPGKGLEWM

GWINTYTGEPTYADKFKDRFTFSLETSASTVYMELTSLTSDDTAVYYC

ARERGDAMDYWGQGTLVTVSSASTKGPSVFPLAPSSKSTSGGTAALGC

LVKDYFSEPVTVSWNSGALTSGVHTFPAVLQSSGLYSLSSVVTVPSSS

LGTQTYICNVNHKPSNTKVDKKVEPKSCTS.
```

At the C-terminus, an inter-chain disulfide bridge is formed between the two constant domains.

The antibodies or antibody derivatives of the present invention can have affinities to human TNFα with dissociation constants $K_d$ in a range of 0.8-10,000 nM. In a preferred embodiment of the present invention the $K_d$ is ≤10 nM. The affinity of an antibody for an antigen can be determined experimentally using a suitable method (Berzofsky et al. "Antibody-Antigen Interactions", in *Fundamental Immunology*, Paul, W. E., Ed, Raven Press: New York, N.Y. (1992); Kuby, J. *Immunology*, W.H. Freeman and Company: New York, N.Y.) and methods described therein.

In one aspect of the present invention the antibodies or antibody derivatives, especially the scFv or Fab fragments, are labeled. Detectable labeling of a TNFα-specific antibody or antibody derivative can be accomplished by linking it to an enzyme for use in an enzyme immunoassay (EIA) or enzyme-linked immunosorbent assay (ELISA), which are methods well known to the person skilled in the art (for example Current Protocols in Immunology, Coligan et al. Eds, John Wiley & Sons, 2005).

By radioactively labeling the TNFα-specific antibodies or antibody derivatives, it is possible to detect TNF-α through the use of radioimmunoassay (RIA) (see for example, Work et al., Laboratory Techniques and Biochemistry in Molecular Biology, North Holland Publishing Company, N.Y. (1978). The radioisotope can be detected by the use of a gamma counter or a scintillation counter or by autoradiography. Particularly useful isotopes are $^{3}H$, $^{131}I$, $^{35}S$, $^{14}C$, and preferably $^{125}I$.

The antibodies or antibody derivatives of the present invention can also be labeled with fluorescent labeling compounds such as fluorescein, isothiocyanate, rhodamine, phycoerythrin, phycocyanin, allophycocyanin, o-phthaldehyde and fluorescamine, or with chemiluminescent compounds such as luminol, isoluminol, theromatic acridinium ester, imidazol acridinium salt and oxalate ester.

Labeling and detection protocols are well known to the person skilled in the art. For example, they are available from *Using Antibodies: A Laboratory Manual: Portable Protocol NO. I (Harlow, E. and Lane, D.,* 1998).

Labeled antibodies or antibody derivatives of the present invention are useful for diagnostic purposes, in particular detection of TNFα in a biological sample removed from a patient. Any sample containing TNFα can be used, e.g. biological fluids like blood, serum, lymph, urine, inflammatory exudate, cerebrospinal fluid, amniotic fluid, a tissue extract or homogenate, and the like, or histological specimens for in situ detection.

PHARMACEUTICAL PREPARATIONS

Definitions: The term "pharmaceutical formulation" refers to preparations which are in such form as to permit the biological activity of the antibody or antibody derivative to be unequivocally effective, and which contain no additional components which are toxic to the subjects to which the formulation would be administered. "Pharmaceutically acceptable" excipients (vehicles, additives) are those which can reasonably be administered to a subject mammal to provide an effective dose of the active ingredient employed.

A "stable" formulation is one in which the antibody or antibody derivative therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at room temperature (about 30° C.) or at 40° C. for at least 1 month and/or stable at about 2-8° C. for at least 1 year for at least 2 years. Furthermore, the formulation is preferably stable following freezing (to, e.g., −70° C.) and thawing of the formulation.

An antibody or antibody derivative "retains its physical stability" in a pharmaceutical formulation if it shows no signs of aggregation, precipitation and/or denaturation upon visual examination of color and/or clarity, or as measured by UV light scattering or by size exclusion chromatography.

An antibody or antibody derivative "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

An antibody or antibody derivative "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated herein below.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "polyol" is a substance with multiple hydroxyl groups, and includes sugars (reducing and non-reducing sugars), sugar alcohols and sugar acids. Preferred polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "non-reducing sugar" is one which does not have these properties of a reducing sugar. Examples of reducing sugars are fructose, mannose, maltose, lactose, arabinose, xylose, ribose, rhamnose, galactose and glucose. Non-reducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it is desired that the formulation is freeze-thaw stable, the polyol is preferably one which does not crystallize at freezing temperatures (e.g. −20° C.) such that it destabilizes the antibody in the formulation. Non-reducing sugars such as sucrose and trehalose are the preferred polyols herein, with trehalose being preferred over sucrose, because of the superior solution stability of trehalose.

As used herein, "buffer" refers to a buffered solution that resists changes in pH by the action of its acid-base conjugate components. The buffer of this invention has a pH in the range from about 4.5 to about 6.0; preferably from about 4.8 to about 5.5; and most preferably has a pH of about 5.0. Examples of buffers that will control the pH in this range include acetate (e.g. sodium acetate), succinate (such as sodium succinate), gluconate, histidine, citrate and other organic acid buffers. Where a freeze-thaw stable formulation is desired, the buffer is preferably not phosphate.

In a pharmacological sense, in the context of the present invention, a "therapeutically effective amount" of an antibody or antibody derivative refers to an amount effective in the prevention or treatment of a disorder for the treatment of which the antibody or antibody derivative is effective. A "disease/disorder" is any condition that would benefit from treatment with the antibody or antibody derivative. This includes chronic and acute disorders or diseases including those pathological conditions which predispose the mammal to the disorder in question.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

The present invention also provides pharmaceutical compositions comprising one or more antibodies or antibody derivative compounds, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives.

As noted above, other active ingredients may (but need not) be included in the pharmaceutical compositions provided herein.

A carrier is a substance that may be associated with an antibody or antibody derivative prior to administration to a patient, often for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

Pharmaceutical compositions may be formulated for any appropriate manner of administration, including, for example, topical, oral, nasal, rectal or parenteral administration. In certain embodiments, compositions in a form suitable for oral use are preferred. Such forms include, for example, pills, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. The term parenteral as used herein includes subcutaneous, intradermal, intravascular (e.g., intravenous), intramuscular, spinal, intracranial, intrathecal and intraperitoneal injection, as well as any similar injection or infusion technique.

Compositions intended for oral use may be prepared according to any method known to the art for the manufacture of pharmaceutical compositions and may contain one or more agents, such as sweetening agents, flavoring agents, coloring agent, and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil). Aqueous suspensions contain the antibody or antibody derivative in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl or n-propyl p-hydroxybenzoate, one or more coloring agents, one or more flavoring agents, and one or more sweetening agents, such as sucrose or saccharin. Syrups and elixirs may be formulated with sweetening agents, such as glycerol, propylene glycol, sorbitol, or sucrose. Such formulations may also comprise one or more demulcents, preservatives, flavoring agents, and/or coloring agents.

Oily suspensions may be formulated by suspending the active ingredients in a vegetable oil (e.g., arachis oil, olive oil, sesame oil, or coconut oil) or in a mineral oil such as liquid paraffin. The oily suspensions may contain a thickening agent such as beeswax, hard paraffin, or cetyl alcohol. Sweetening agents, such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin), or a mixture thereof. Suitable emulsifying agents include naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate), and condensation products of partial esters derived from fatty acids and hexitol with ethylene oxide (e.g., polyoxyethylene sorbitan monoleate). An emulsion may also comprise one or more sweetening and/or flavoring agents.

The pharmaceutical composition may be prepared as a sterile injectible aqueous or oleaginous suspension in which the modulator, depending on the vehicle and concentration used, is either suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid may be used in the preparation of injectible compositions, and adjuvants such as local anesthetics, preservatives and/or buffering agents can be dissolved in the vehicle.

Pharmaceutical compositions may be formulated as sustained release formulations (i.e., a formulation such as a capsule that effects a slow release of modulator following administration). Such formulations may generally be prepared using well known technology and administered by, for example, oral, rectal, or subcutaneous implantation, or by implantation at the desired target site. Carriers for use within such formulations are biocompatible, and may also be biodegradable; preferably the formulation provides a relatively constant level of modulator release. The amount of an antibody or antibody derivative contained within a sustained release formulation depends upon, for example, the site of implantation, the rate and expected duration of release and the nature of the disease/disorder to be treated or prevented.

Antibody or antibody derivatives provided herein are generally administered in an amount that achieves a concentration in a body fluid (e.g., blood, plasma, serum, CSF, synovial fluid, lymph, cellular interstitial fluid, tears or urine) that is sufficient to detectably bind to TNFα and prevent or inhibit TNFα associated diseases/disorders. A dose is considered to be effective if it results in a discernible patient benefit as described herein. Preferred systemic doses range from about 0.1 mg to about 140 mg per kilogram of body weight per day (about 0.5 mg to about 7 g per patient per day), with oral doses generally being about 5-20 fold higher than intravenous doses. The amount of antibody or antibody derivative that may be combined with the carrier materials to produce a single dosage form will vary depending upon the host treated and the particular mode of administration. Dosage unit forms will generally contain between from about 1 mg to about 500 mg of an active ingredient.

Pharmaceutical compositions may be packaged for treating conditions responsive to an antibody or antibody derivative directed to TNF-α. Packaged pharmaceutical compositions may include a container holding a effective amount of at least one antibody or antibody derivative as described herein and instructions (e.g., labeling) indicating that the contained composition is to be used for treating a disease/disorder responsive to one antibody or antibody derivative following administration in the patient.

The antibodies or antibody derivatives of the present invention can also be chemically modified. Preferred modifying groups are polymers, for example an optionally substituted straight or branched chain polyalkene, polyalkenylene, or polyoxyalkylene polymer or a branched or unbranched polysaccharide. Such effector group may increase the half-live of the antibody in vivo. Particular examples of synthetic polymers include optionally substituted straight or branched chain poly(ethyleneglycol) (PEG), poly(propyleneglycol), poly(vinylalcohol) or derivatives thereof. Particular naturally occurring polymers include lactose, amylose, dextran, glycogen or derivatives thereof. The size of the polymer may be varied as desired, but will generally be in an average molecular weight range from 500 Da to 50000 Da. For local application where the antibody is designed to penetrate tissue, a preferred molecular weight of the polymer is around 5000 Da. The polymer molecule can be attached to the antibody, in particular to the C-terminal end of the Fab fragment heavy chain via a covalently linked hinge peptide as described in WO0194585. Regarding the attachment of PEG moieties, reference is made to "Poly(ethyleneglycol) Chemistry, Biotechnological and Biomedical Applications", 1992, J. Milton Harris (ed), Plenum Press, New York and "Bioconjugation Protein Coupling Techniques for the Biomedical Sciences", 1998, M. Aslam and A. Dent, Grove Publishers, New York.

Preparation of the Formulation

After preparation of the antibody or antibody derivative of interest as described above, the pharmaceutical formulation comprising it is prepared. The antibody to be formulated has not been subjected to prior lyophilization and the formulation of interest herein is an aqueous formulation. Preferably the antibody or antibody derivative in the formulation is an antibody fragment, such as an scFv. The therapeutically effective amount of antibody present in the formulation is determined by taking into account the desired dose volumes and mode(s) of administration, for example. From about 0.1 mg/ml to about 50 mg/ml, preferably from about 0.5 mg/ml to about 25 mg/ml and most preferably from about 2 mg/ml to about 10 mg/ml is an exemplary antibody concentration in the formulation.

An aqueous formulation is prepared comprising the antibody or antibody derivative in a pH-buffered solution The buffer of this invention has a pH in the range from about 4.5 to about 6.0, preferably from about 4.8 to about 5.5, and most preferably has a pH of about 5.0. Examples of buffers that will control the pH within this range include acetate (e.g. sodium acetate), succinate (such as sodium succinate), gluconate, histidine, citrate and other organic acid buffers. The buffer concentration can be from about 1 mM to about 50 mM, preferably from about 5 mM to about 30 mM, depending, for example, on the buffer and the desired isotonicity of the formulation. The preferred buffer is sodium acetate (about 10 mM), pH 5.0.

A polyol, which acts as a tonicifier and may stabilize the antibody, is included in the formulation. In preferred embodiments, the formulation does not contain a tonicifying amount of a salt such as sodium chloride, as this may cause the antibody or antibody derivative to precipitate and/or may result in oxidation at low pH. In preferred embodiments, the polyol is a non-reducing sugar, such as sucrose or trehalose. The polyol is added to the formulation in an amount which may vary with respect to the desired isotonicity of the formulation. Preferably the aqueous formulation is isotonic, in which case suitable concentrations of the polyol in the formulation are in the range from about 1% to about 15% w/v, preferably in the range from about 2% to about 10% w/v, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant is also added to the antibody or antibody derivative formulation. Exemplary surfactants include nonionic surfactants such as polysorbates (e.g. polysorbates 20, 80 etc) or poloxamers (e.g. poloxamer 188). The amount of surfactant added is such that it reduces aggregation of the formulated antibody/antibody derivative and/or minimizes the formation of particulates in the formulation and/or reduces adsorption. For example, the surfactant may be present in the formulation in an amount from about 0.001% to about 0.5%, preferably from about 0.005% to about 0.2% and most preferably from about 0.01% to about 0.1%.

In one embodiment, the formulation contains the above-identified agents (i.e. antibody or antibody derivative, buffer, polyol and surfactant) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, most preferably from about 0.5% to about 1%. One or more other pharmaceutically acceptable carriers, excipients or stabilizers such as those described in Remington's Pharmaceutical Sciences 21st edition, Osol, A. Ed. (2006) may be included in the formulation provided that they do not adversely affect the desired characteristics of the formulation. Acceptable carriers, excipients or stabilizers are non-toxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The formulations to be used for in vivo administration must be sterile. This is readily accomplished by filtration through sterile filtration membranes, prior to, or following, preparation of the formulation.

Administration of the Formulation

The formulation is administered to a mammal in need of treatment with the antibody, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In preferred embodiments, the formulation is administered to the mammal by intravenous administration. For such purposes, the formulation may be injected using a syringe or via an IV line, for example.

The appropriate dosage ("therapeutically effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody or antibody derivative is suitably administered to the patent at one time or over a series of treatments and may be administered to the patent at any time from diagnosis onwards. The antibody or antibody derivative may be administered as the sole treatment or in conjunction with other drugs or therapies useful in treating the condition in question.

As a general proposition, the therapeutically effective amount of the antibody or antibody derivative administered will be in the range of about 0.1 to about 50 mg/kg of patent body weight whether by one or more administrations, with the typical range of antibody used being about 0.3 to about 20 mg/kg, more preferably about 0.3 to about 15 mg/kg, administered daily, for example. However, other dosage regimens may be useful. The progress of this therapy is easily monitored by conventional techniques.

Articles of Manufacture

In another embodiment of the invention, an article of manufacture is provided comprising a container which holds the aqueous pharmaceutical formulation of the present invention and optionally provides instructions for its use. Suitable containers include, for example, bottles, vials and syringes. The container may be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

Generating the Antibodies of the Present Invention

The antibodies or antibody derivatives of the present invention may be generated using routine techniques in the field of recombinant genetics. Knowing the sequences of the polypeptides, the cDNAs encoding them can be generated by gene synthesis (www.genscript.com). These cDNAs can be cloned into suitable vector plasmids. Once the DNA encoding a VL and/or a VH domain are obtained, site directed mutagenesis, for example by PCR using mutagenic primers, can be performed to obtain various derivatives. The best "starting" sequence can be chosen depending on the number of alterations desired in the VL and/or VH sequences. A preferred sequence is the TB-A sequences and its derivatives, e.g. scFv sequences or Fab fusion peptide sequences, may be chosen as templates for PCR driven mutagenesis and/or cloning.

Standard cloning and mutagenesis techniques well known to the person skilled in the art can be used to attach linkers, shuffle domains or construct fusions for the production of Fab fragments. Basic protocols disclosing the general methods of this invention are described in *Molecular Cloning, A Laboratory Manual* (Sambrook & Russell, 3$^{rd}$ ed. 2001) and in *Current Protocols in Molecular Biology* (Ausubel et al., 1999).

The DNA sequence harboring a gene encoding a scFv polypeptide, or in the case of Fab fragments, encoding either two separate genes or a bi-cistronic operon comprising the two genes for the VL-Cκ and the VH-CH1 fusions (FIG. 2) are cloned in a suitable expression vector, preferably one with an inducible promoter. Care must be taken that in front of each gene an appropriate ribosome binding site (RBS in FIG. 2) is present that ensures translation. It is to be understood that the antibodies of the present invention comprise the disclosed sequences rather than they consist of them. For example, cloning strategies may require that a construct is made from which an antibody with one or a few additional residues at the N-terminal end are present. Specifically, the methionine derived from the start codon may be present in the final protein in cases where it has not been cleaved posttranslationally. Most of the constructs for scFv antibodies give rise to an additional alanine at the N-terminal end. In a preferred embodiment of the present invention, an expression vector for periplasmic expression in *E. coli* is chosen (Krebber, 1997). Said vector comprises a promoter in front of a cleavable signal sequence. The coding sequence for the antibody peptide is then fused in frame to the cleavable signal sequence. This allows the targeting of the expressed polypeptide to the bacterial periplasm where the signal sequence is cleaved. The antibody is then folded. In the case of the Fab fragments, both the VL-Cκ and the VH-CH1 fusions peptides must be linked to an export signal. The covalent S—S bond is formed at the C-terminal cysteines after the peptides have reached the periplasm. If cytoplasmic expression of antibodies is preferred, said antibodies usually can be obtained at high yields from inclusion bodies, which can be easily separated from other cellular fragments and protein. In this case the inclusion bodies are solubilized in a denaturing agent such as e.g. guaridine hydrochloride (GndHCl) and then refolded by renaturation procedures well known to those skilled in the art. Plasmids expressing the scFv or Fab polypeptides are introduced into a suitable host, preferably a bacterial, yeast or mammalian cell, most preferably a suitable *E. coli* strain as for example JM83 for periplasmic expression or BL21 for expression in inclusion bodies. The polypeptide can be harvested either from the periplasm or form inclusion bodies and purified using standard techniques such as ion exchange chromatography, reversed phase chromatography, affinity chromatography and/or gel filtration known to the person skilled in the art.

The antibodies or antibody derivatives of the present invention can be characterized with respect to yield, solubility and stability in vitro. Binding capacities towards TNFα, preferably towards human TNFα, can be tested in vitro by ELISA or surface plasmon resonance (BIACore), using recombinant human TNFα as described in WO9729131, the latter method also allowing to determine the $k_{off}$-rate constant, which should preferably be less than $10^{-3}$ $s^{-1}$. $K_d$ values of ≤10 nM are preferred.

In vivo neutralizing activity of an antibody or antibody derivative of the present invention can be estimated using the L929 cytotoxicity assay. Human recombinant TNFα exerts a cytotoxic effect towards cultured mouse L929 fibroblast cells in a concentration-dependent manner. This TNFα-induced cytotoxicity can be inhibited by TNFα neutralizing antibodies (Miring, 1994). A preferred $IC_{50}$ value corresponding to a half-maximal inhibitor concentration is ≤100 ng $ml^{-1}$.

As TNFα has a proven pathophysiological role in various human diseases, in particular inflammatory disorders, immune and immune-regulated disorders, infections causing septic, endotoxic and cardiovascular shock, neurodegenerative diseases, and malignant diseases. As TNFα is suspected to play a disease-relevant role in a steadily growing number of additional human diseases, it is difficult to give a comprehensive list of indications that also ensures a complete representation of the spectrum of clinical applications for TNFα inhibitors in the future. Therefore, the antibodies or antibody derivatives of the present invention can be applied to treat the diseases listed in the following catalogue, which is not to be considered as a complete or exclusive list. Other diseases not mentioned specifically, which directly or indirectly are influenced by TNFα, are also included.

Autoimmune or Chronic Inflammation:

Chronic and/or autoimmune states of inflammation in general, immune mediated inflammatory disorders in general, inflammatory CNS disease, inflammatory diseases affecting the eye, joint, skin, mucuous membranes, central nervous system, gastrointestinal tract, urinary tract or lung, states of uveitis in general, retinitis, HLA-B27+ uveitis, Behcet's disease, dry eye syndrome, glaucoma, Sjögren syndrome, diabetes mellitus (incl. diabetic neuropathy), insulin resistance, states of arthritis in general, rheumatoid arthritis, osteoarthritis, reactive arthritis and Reiter's syndrome, juvenile arthritis, ankylosing spondylitis, multiple sclerosis, Guillain-Barre syndrome, myasthenia gravis, amyotrophic lateral sclerosis, sarcoidosis, glomerulonephritis, chronic kidney disease, cystitis, Psoriasis (incl. psoriatic arthritis), hidradenitis suppurativa, panniculitis, pyoderma gangrenosum, SAPHO syndrome (synovitis, acne, pustulosis, hyperostosis and osteitis), acne, Sweet's syndrome, pemphigus, Crohn's disease (incl. extraintestinal manifestastations), ulcerative colitis, asthma bronchiale, hypersensitivity pneumonitis, general allergies, allergic rhinitis, allergic sinusitis, chronic obstructive pulmonary disease (COPD), lung fibrosis, Wegener's granulomatosis, Kawasaki syndrome, Giant cell arteritis, Churg-Strauss vasculitis, polyarteritis nodosa, burns, graft versus host disease, host versus graft reactions, rejection episodes following organ or bone marrow transplantation, sytemic and local states of vasculitis in general, systemic and discoid lupus erythematodes, polymyositis and dermatomyositis, sclerodermia, pre-eclampsia, acute and chronic pancreatitis, viral hepatitis, alcoholic hepatitis.

Acute Inflammation and/or Prevention of Postsurgical or Posttraumatic Inflammation and Pain:

Prevention of postsurgical inflammation in general, eye surgery (e.g. cataract (eye lens replacement) or glaucoma surgery), joint surgery (incl. arthroscopic surgery), surgery at joint-related structures (e.g. ligaments), oral and/or dental surgery, minimally invasive cardiovascular procedures (e.g. PTCA, atherectomy, stent placement), laparoscopic and/or endoscopic intra-abdominal and gynecological procedures, endoscopic urological procedures (e.g. prostate surgery, ureteroscopy, cystoscopy, interstitial cystitis), perioperative inflammation (prevention) in general.

Neurological and Neurodegenarative Diseases:

Alzheimer disease, Parkinson's disease, Huntington's disease, Bell' palsy, Creutzfeld-Jakob disease.

Cancer:

Cancer-related osteolysis, cancer-related inflammation, cancer-related pain, cancer-related cachexia, bone metastases.

Pain:

Acute and chronic forms of pain, irrespective whether these are caused by central or peripheral effects of TNFα and whether they are classified as inflammatory, nociceptive or neuropathic forms of pain, sciatica, low back pain, carpal tunnel syndrome, complex regional pain syndrome (CRPS), gout, postherpetic neuralgia, fibromyalgia, local pain states, chronic pain syndroms due to metastatic tumor, dismenorrhea.

Infection:

Bacterial, viral or fungal sepsis, tuberculosis, AIDS.

Cardiovascular Disease:

Atherosclerosis, coronary artery disease, hypertension, dyslipidemia, heart insufficiency and chronic heart failure.

In a preferred embodiment of the present invention, treatment of osteoarthritis or uveitis or inflammatory bowel disease can be achieved with the antibodies or antibody derivatives of the present invention.

The present invention also provides a pharmaceutical composition comprising an antibody or antibody derivative molecule of the present invention in combination with a pharmaceutically acceptable excipient, diluent or carrier.

The pharmaceutical composition should preferably comprise a therapeutically effective amount of the antibody of the present invention, i.e. an amount of said antibody that is needed to treat, ameliorate or prevent the TNFα-related disease or condition, or to exhibit a detectable therapeutic or preventive effect. The therapeutically effective dose can be estimated either in cell culture assays or in animal models, usually in rodents, rabbits, dogs, pigs or primates. The animal model may also be used to determine the appropriate concentration range and route of administration. A suitable animal model to observe an effect of the antibody or antibody derivative of the present invention is a rat model for acute monoarthritis (Bolon et al. (2004), Vet. Pathol. 41:235-243. Human TNFα is injected intraarticularly into the knee joint of a rat, leading to an acute, self-limiting monoarthritis in the injected joint. Bioactivity of an anti-TNFα antibody (derivative) can be quantified by reduction of TNFα-induced knee joint swelling and or reduction of histological parameters of inflammation.

As the antibodies or antibody derivatives of the present invention are highly soluble, high antibody concentrations (60 mg $ml^{-1}$ or more) enable the use of small application volumes.

The antibody or antibody derivative of the present invention may be utilised in any therapy where it is desired to reduce the level of biological active TNFα present in the human or animal body. The TNFα may be circulating in the body or be present at an undesirably high level localised at a particular site in the body. The present invention provides modes for systemic as well as local applications in general, which include, but are not limited to the following ones: peroral application, intravenous, subcutaneous, intramuscular, intraarticular, intravitreal, intradermal, or intraparenchymal injection, aerosol inhalation, topical application to the skin, to mucous membranes or to eye, systemic or local release via implantable minipump or local release via implantable formulation/device allowing for retarded release, topical application to serosal surfaces, intrathecal or intraventricular application, oral application in formulations allowing for controlled intralumenal release in selected parts of the gastrointestinal tract, localized intravasal release from adequate formulation/devices (e.g. stents), local delivery to urinary cyst, localized intralumenal release (e.g. to biliary tract, ureter), or local delivery through endoscopic devices, or release from contact lenses (contacts). A preferred application is a local one such as intraarticular injection or topic application e.g. into the eye. For both preferred applications, the antibody of the present invention needs to be in solution.

The present invention also reveals the use of the antibody or antibody derivative of the present invention for the production of a medicament for the treatment of TNFα associated diseases. In this case, the antibody or antibody derivative is comprised in a therapeutic composition. Said composition is used as a medicament, most preferably for the prevention or therapy of TNFα related diseases.

In another aspect the scFv antibodies of the present invention are used in gene therapy, in particular in adoptive cellular gene therapy. Autoimmune disorders represent inappropriate immune responses directed at self-tissue. Antigen-specific CD4+ T cells and antigen-presenting dendritic cells (DCs) are important mediators in the pathogenesis of auto-immune disease and thus are ideal candidates for adoptive cellular gene therapy, an ex vivo approach to therapeutic gene transfer. Using retrovirally transduced cells and luciferase bioluminescence, Tarner et al. (2003, Ann. N.Y. Acad. Sci. 998:512-519) have demonstrated that primary T cells, T cell hybridomas, and DCs rapidly and preferentially home to the sites of inflammation in animal models of multiple sclerosis, arthritis, and diabetes. These cells, transduced with retroviral vectors that drive expression of various “regulatory proteins” such as interleukins and anti-TNF scFv, deliver these immunoregulatory proteins to the inflamed lesions, providing therapy for experimental autoimmune encephalitis, collagen-induced arthritis, and nonobese diabetic mice. The stable and soluble frameworks of the antibodies or antibody derivatives of the present inventions are particularly suitable for intracellular delivery of the antigen, for example when the antibody or antibody derivative is expressed from a transgene carried by a suitable retroviral vector. Adoptive cellular gene therapy leads to localized expression and secretion of the anti-TNFα scFv. Smith et al. (2003) have demonstrated that scFvs derived from a TNFα neutralizing monoclonal antibody (i) can neutralize TNFα in vitro and (ii) change the cytokine expression pattern in mice suffering from collagen-induced arthritis locally in the joints, but not systemically. Alternatively, direct systemic or local injection of suitable vectors (e.g. viruses) allowing for continuous expression of an anti-TNFα scFv antibody, is considered as another possible gene therapy approach.

The sequences of the present invention are the following ones:

VL of TB-A

SEQ ID NO: 1

```
DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKR
```

VH of TB-A

SEQ ID NO: 2

```
QVQLVQSGAEVKKPGASVKVSCTASGYTFTHYGMNWVRQAPGKGLEWMGWINTYT

GEPTYADKFKDRFTFSLETSASTVYMELTSLTSDDTAVYYCARERGDAMDYWGQGTL

VTVSS
```

VL of TB-B

SEQ ID NO: 3

```
DIVLTQSPSSLSASVGDRVTLTCTASQSVSNDVVWYQQRPGKAPKRLIYSAFNRYTGVP

SRFSGSGSGTEFTLTISSLQPEDVAVYYCQQDYNSPRTFGQGTKLEVKR
```

VH of TB-B

SEQ ID NO: 4

```
QVQLVQSGAEVKKPGASVKVSCTASGYSFTHYGMNWVRQAPGQGLEWMGWINTYT
```

-continued

GEPTYADKFKDRVTLTRDTSIGTVYMELTSLTSDDTAVYYCARERGDAMDYWGQGTL

VTVSS

VL of FW2.3

SEQ ID NO: 5

DIVLTQSPSSLSASVGDRVTLTCRASQGIRNELAWYQQRPGKAPKRLIYAGSILQSGVPS

RFSGSGSGTEFTLTISSLQPEDVAVYYCQQYYSLPYMFGQGTKLEVKR

VH of FW2.3

SEQ ID NO: 6

QVQLVQSGAEVKKPGASVKVSCTASGYSFTGYFLHWVRQAPGQGLEWMGRINPDSGD

TIYAQKFQDRVTLTRDTSIGTVYMELTSLTSDDTAVYYCARVPRGTYLDPWDYFDYW

GQGTLVTVSS

VL of TB_L2

SEQ ID NO: 7

DIVMTQSPSSLSASVGDRVTLTCTASQSVSNDVVWYQQRPGKAPKLLIYAGSILQSGVP

SRFSGRGYGTDFTLTISSLQPEDVAVYYCQQDYNSPRTFGQGTKLEVKR

VL of TB_L3

SEQ ID NO: 8

DIVMTQSPSSLSASVGDRVTLTCTASQSVSNDVVWYQQRPGKAPKLLIYSAFNRYTGV

PSRFSGRGYGTDFTLTISSLQPEDVAVYYCQQYYSLPYMFGQGTKLEVKR

VH of TB_H2

SEQ ID NO: 9

QVQLVQSGAEVKKPGASVKVSCTASGYTFTHYGMNWVRQAPGKGLEWMGRINPDSG

DTIYAQKFQDRFTFSLETSASTVYMELTSLTSDDTAVYYCARERGDAMDYWGQGTLV

TVSS

Linker

SEQ ID NO: 10

GGGGSGGGGSGGGGSGGGGS

VL of TB-B R46L

SEQ ID NO: 11

DIVLTQSPSSLSASVGDRVTLTCTASQSVSNDVVWYQQRPGKAPKLLIYSAFNRYTGVP

SRFSGSGSGTEFTLTISSLQPEDVAVYYCQQDYNSPRTFGQGTKLEVKR

TB-AB

SEQ ID NO: 12

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYSFTHYGMNWVRQAPGQGL

EWMGWINTYTGEPTYADKFKDRVTLTRDTSIGTVYMELTSLTSDDTAVYYCARERGD

AMDYWGQGTLVTVSS

TB-BA

SEQ ID NO: 13

DIVLTQSPSSLSASVGDRVTLTCTASQSVSNDVVWYQQRPGKAPKRLIYSAFNRYTGVP

SRFSGSGSGTEFTLTISSLQPEDVAVYYCQQDYNSPRTFGQGTKLEVKRGGGGSGGGGS

GGGGSGGGGSQVQLVQSGAEVKKPGASVKVSCTASGYTFTHYGMNWVRQAPGKGLE

WMGWINTYTGEPTYADKFKDRFTFSLETSASTVYMELTSLTSDDTAVYYCARERGDA

MDYWGQGTLVTVSS

Cκ of Fab

SEQ ID NO: 14

TVAAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC

CH1 of Fab

SEQ ID NO: 15

ASTKGPSVFPLAPSSKSTSGGTAALGCLVKDYFSEPVTVSWNSGALTSGVHTFPAVLQS

-continued

SGLYSLSSVVTVPSSSLGTQTYICNVNHKPSNTKVDKKVEPKSCTS

VL of TB-wt

SEQ ID NO: 16

DIVMTQTPKFLLVSAGDRVTITCTASQSVSNDVVWYQQKPGQSPKMLMYSAFNRYTG

VPDRFTGRGYGTDFTFTISSVQAEDLAVYFCQQDYNSPRTFGGGTKLEIKR

VH of TB-wt

SEQ ID NO: 17

QIQLVQSGPELKKPGETVKISCKASGYTFTHYGMNWVKQAPGKGLKWMGWINTYTG

EPTYADDFKEHFAFSLETSASTVFLQINNLKNEDTATYFCARERGDAMDYWGQGTSV

TVSS

TB-A H_K43Q, also named TB-A H43

SEQ ID NO: 18

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGQGL

EWMGWINTYTGEPTYADKFKDRFTFSLETSASTVYMELTSLTSDDTAVYYCARERGD

AMDYWGQGTLVTVSS

TB-A H_F68V, also named TB-A H68

SEQ ID NO: 19

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWMGWINTYTGEPTYADKFKDRVTFSLETSASTVYMELTSLTSDDTAVYYCARERGD

AMDYWGQGTLVTVSS

TB-A H_F70L/L72R, also named TB-A H70/72

SEQ ID NO: 20

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWMGWINTYTGEPTYADKFKDRFTLSRETSASTVYMELTSLTSDDTAVYYCARERGD

AMDYWGQGTLVTVSS

TB-A H_A76I/S77G, also named TB-A H76/77

SEQ ID NO: 21,

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWMGWINTYTGEPTYADKFKDRFTFSLETSIGTVYMELTSLTSDDTAVYYCARERGD

AMDYWGQGTLVTVSS

TB-A L_L46R, also named TB-A L46

SEQ ID NO: 22

DIVMTQSPSSLSASVGDRVTLTCTASQSVSNDVVWYQQRPGKAPKRLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWMGWINTYTGEPTYADKFKDRFTFSLETSASTVYMELTSLTSDDTAVYYCARERGD

AMDYWGQGTLVTVSS

TB-A L_R65S, also named TB-A L65

SEQ ID NO: 23

DIVMTQSPSSLSASVGDRVTLTCTASQSVSNDVVWYQQRPGKAPKLLIYSAFNRYTGV

-continued

PSRFSGSGYGTDFTLTISSLQPEDVAVYYCQQDYNSPRTFGQGTKLEVKRGGGGSGGGG

SGGGGSGGGGSQVQLVQSGAEVKKPGASVKVSCTASGYTFTHYGMNWVRQAPGKGLE

WMGWINTYTGEPTYADKEKDRFTESLETSASTVYMELTSLTSDDTAVYYCARERGDA

MDYWGQGTLVTVSS

TB-A L_Y67S, also named TB-A L67

SEQ ID NO: 24

DIVMTQSPSSLSASVGDRVTLTCTASQSVSNDVVWYQQRPGKAPKLLIYSAFNRYTGV

PSRFSGRGSGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWMGWINTYTGEPTYADKFKDRFTFSLETSASTVYMELTSLTSDDTAVYYCARERGD

AMDYWGQGTLVTVSS

VH of TB-A with D66G

SEQ ID NO: 25

QVQLVQSGAEVKKPGASVKVSCTASGYTETHYGMNWVRQAPGKGLEWMGWINTYT

GEPTYADKFKGRFTFSLETSASTVYMELTSLTSDDTAVYYCARERGDAMDYWGQGTL

VTVSS

VL of TB-A with V83F

SEQ ID NO: 26

DIVMTQSPSSLSASVGDRVTLTCTASQSVSNDVVWYQQRPGKAPKLLIYSAFNRYTGV

PSRFSGRGYGTDFTLTISSLQPEDFAVYYCQQDYNSPRTFGQGTKLEVKR

VL of TB-A with V83A

SEQ ID NO: 27

DIVMTQSPSSLSASVGDRVTLTCTASQSVSNDVVWYQQRPGKAPKLLIYSAFNRYTGV

PSRFSGRGYGTDFTLTISSLQPEDAAVYYCQQDYNSPRTFGQGTKLEVKR

VH of TB-A H43/70/71/73/77

SEQ ID NO: 28

QVQLVQSGAEVKKPGASVKVSCTASGYTETHYGMNWVRQAPGQGLEWMGWINTYT

GEPTYADKFKDRFTLTLDTSAGTVYMELTSLTSDDTAVYYCARERGDAMDYWGQGT

LVTVSS

VH of TB-A H43/70/71

SEQ ID NO: 29

QVQLVQSGAEVKKPGASVKVSCTASGYTETHYGMNWVRQAPGQGLEWMGWINTYT

GEPTYADKFKDRFTLTLETSASTVYMELTSLTSDDTAVYYCARERGDAMDYWGQGTL

VTVSS

VH of TB-A H11/16/43/66/70/71/73/77/93/112

SEQ ID NO: 30

QVQLVQSGAEDKKPGGSVKVSCTASGYTFTHYGMNWVRQAPGQGLEWMGWINTYT

GEPTYADKFKGRFTLTLDTSAGTVYMELTSLTSDDTATYYCARERGDAMDYWGQGT

SVTVSS

TB-A H_M48L/F68I

SEQ ID NO: 31

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWLGWINTYTGEPTYADKFKDRITFSLETSASTVYMELTSLTSDDTAVYYCARERGDA

MDYWGQGTLVTVSS

TB-A L_V83E H_V79A

SEQ ID NO: 32

DIVMTQSPSSLSASVGDRVTLTCTASQSVSNDVVWYQQRPGKAPKLLIYSAFNRYTGV

PSRFSGRGYGTDFTLTISSLQPEDEAVYYCQQDYNSPRTFGQGTKLEVKRGGGGSGGG

-continued

GSGGGGSGGGGSQVQLVQSGAEVKKPGASVKVSCTASGYTFTHYGMNWVRQAPGKGL

EWMGWINTYTGEPTYADKFKDRFTFSLETSASTAYMELTSLTSDDTAVYYCARERGD

AMDYWGQGTLVTVSS

TB-A Linker_G2R H_F68L

SEQ ID NO: 33

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGRGGSGGG

GSGGGGSGGGGSQVQLVQSGAEVKKPGASVKVSCTASGYTFTHYGMNWVRQAPGKGL

EWMGWINTYTGEPTYADKFKDRLTFSLETSASTVYMELTSLTSDDTAVYYCARERGD

AMDYWGQGTLVTVSS

TB-A H_K43R/F68I

SEQ ID NO: 34

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGRGL

EWMGWINTYTGEPTYADKFKDRITFSLETSASTVYMELTSLTSDDTAVYYCARERGD

AMDYWGQGTLVTVSS

TB-A H_F68L

SEQ ID NO: 35

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWMGWINTYTGEPTYADKFKDRLTFSLETSASTVYMELTSLTSDDTAVYYCARERGD

AMDYWGQGTLVTVSS

TB-A H_F68A

SEQ ID NO: 36

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWMGWINTYTGEPTYADKFKDRATFSLETSASTVYMELTSLTSDDTAVYYCARERGD

AMDYWGQGTLVTVSS

TB-A H_F68V/F70L

SEQ ID NO: 37

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWMGWINTYTGEPTYADKFKDRVTLSLETSASTVYMELTSLTSDDTAVYYCARERGD

AMDYWGQGTLVTVSS

TB-A H_F70L

SEQ ID NO: 38

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWMGWINTYTGEPTYADKFKDRFTLSLETSASTVYMELTSLTSDDTAVYYCARERGD

AMDYWGQGTLVTVSS

Linker G2R

-continued

SEQ ID NO: 39

GRGGSGGGGSGGGGSGGGGS

TB-A

SEQ ID NO: 40

DIVMTQSPSSLSASVGDRVTLTCTASQSVSNDVVWYQQRPGKAPKLLIYSAFNRYTGV

PSRFSGRGYGTDFTLTISSLQPEDVAVYYCQQDYNSPRTFGQGTKLEVKRGGGGSGGG

GSGGGGSGGGGSQVQLVQSGAEVKKPGASVKVSCTASGYTFTHYGMNWVRQAPGKGL

EWMGWINTYTGEPTYADKFKDRFTFSLETSASTVYMELTSLTSDDTAVYYCARERGD

AMDYWGQGTLVTVSS

The invention will be more fully understood by reference to the following examples. They should not, however, be construed as limiting the scope of the invention. All literature and patent citations are incorporated herein by reference.

Experiment 1

Construction of scFv Antibodies

The starting material for the generation of humanised anti-human TNFα antibodies or antibody derivatives, such as single-chain fragments (scFv) or Fab fragments, was the murine monoclonal antibody Di62. The sequences of the variable region of the light chain and the heavy chain are disclosed in Döring et al. (1994, *Mol. Immunol.* 31:1059-1067). The properties of this monoclonal antibody are also discussed in the same publication. Briefly, Di62 specifically binds to human TNFα in a concentration-dependent manner. It is a high affinity antibody (Kd=0.4 nM) and can block TNFα binding to its receptor. In addition, Di62 inhibits human TNFα-induced cytotoxicity in mouse L929 cells.

Based on its published sequence Di62 was constructed in the form of a single-chain antibody derivative (scFv) in the orientation VL-linker-VH, in which the linker sequence is composed of four repeats of four glycine and one serine residue $(Gly_4Ser)_4$. Herein, this scFv is referred to as TB-wt, with a VL of SEQ ID NO:16 and a VH of SEQ ID NO:17.

To humanise this antibody derivative for the purpose of a) render it more similar to human sequences in order to minimise potential immunogenicity, and b) render it more stable and soluble, TB-wt CDR sequences were grafted on stable and soluble human frameworks (Auf der Maur et al. (2001), FEBS Lett. 508:407-412; Auf der Maur et al. (2004), Methods 34:215-224). The human VL-kappa subgroup I and VH subgroup I were identified as nearest human subfamily. The appropriate acceptor framework was chosen from a pool of human VL and VH sequences, selected for advantageous biochemical and biophysical properties, such as for example stability, solubility, and expression properties (Auf der Maur, et al. (2001), FEBS Lett. 508:407-412; Auf der Maur, et al. (2004), Methods 34:215-224). The isolation and properties of these antibody frameworks are described in WO03097697/EP1506236. From this pool, a single-chain antibody framework with undefined antigen binding properties was identified as suitable acceptor. This acceptor consists of a human VL-kappa I domain (SEQ ID NO:14) in combination with a human VHI domain (SEQ ID NO:15). Herein, this acceptor framework is referred to as FW2.3. Among 81 VL framework residues, TB-wt and FW2.3 share 55 identical amino acid residues, which amounts to 67% identity. Among the 87 VH framework residues, TB-wt and FW2.3 have 55 identical residues, corresponding to 63% identity. Both single-chain antibody derivatives have identical CDR lengths, apart from the VH-CDR3, which is longer in FW2.3. The amino acid composition within the CDR residues is different for both scFvs. Various methods for the humanisation of antibody variable domains are described (Riechmann et al. (1998), Nature 332:323-327; Padlan, E. A. (1991). Mol. Immunol. 28:489-498; Roguska et al. (1994), Proc. Natl. Acad. Sci. USA 91:969-973; Gonzales et al. (2005), Tumor Biol. 26:31-43; Ewert, S., et al. (2004), Methods 34:184-199). The minimal approach, namely the conservative transfer of all mouse CDR loops from TB-wt onto FW2.3 was carried out first. The resulting scFv is referred to as TB-B and has the VL sequence of SEQ ID NO:3 and the VH sequence of SEQ ID NO:4. The CDR-loops in TB-wt were defined according to the Kabat numbering scheme (Kabat et al. (1991), Sequences of Proteins of Immunological Interest, 5th Ed, Natl. Inst. Health, Bethesda, Md.) and confine the following residues (see FIG. 1):

VL

CDR1: L24-L34 (same Kabat numbering)

CDR2: L50-L56 (same Kabat numbering)

CDR3: L89-L97 (same Kabat numbering)

VH

CDR1: H31-H35 (same Kabat numbering)

CDR2: H50-H66 (Kabat numbering H50-H65)

CDR3: H99-H106 (Kabat numbering H95-H102).

This antibody was unable to bind TNFα efficiently (FIG. 4A). The next step was to determine which residue or residues from these components should be substituted to optimise the properties of the resulting humanised antibody.

Since substitution of human amino acid residues with other amino acids should be minimised because introduction of foreign amino acid sequences increases the risk of immunogenicity of the antibody or antibody derivative in humans (Gonzales et al. (2005), Tumor Biol. 26:31-43), several variants were constructed. One of said variants—herein referred to as TB-B L46 (VL SEQ ID NO:11; VH SEQ ID NO:4) was constructed with the aim to minimize the risk of being immunogenic but still showing sufficient binding activity. This variant is based on TB-B and contains one single amino acid change at position 46 in VL, namely R→L. This amino acid is located within the upper core of the light chain and takes part in the dimer interface. It is involved in defining the conformation of L-CDR1 and has an influence on VH/VL packing. It was reported that a leucine residue is favoured at this particular position (PCT/US03/19333). In contrast to TB-B, the scFv TB-B L46 retains some TNFα-specific binding (FIG. 4A; $K_d$≈100 nM)).

In order to further improve the TNFα-binding activity, one or more further exchanges were made at one or more of the VL residues 4, 46, 65, 67, 70, and/or VH residues 28, 43, 68, 70, 71, 72, 73, 76, 77. Herein, the variant with exchanges in all positions is referred to as TB-A (VL SEQ ID NO:1; VH SEQ ID NO:2).

Furthermore, regarding particular anti-TNFα antibodies of the present invention, competition assays with peptides derived from L-CDR1 and L-CDR2 showed that both CDR loops are important for the binding of the scFv to the antigen (Döring et al. (1994), Mol. Immunol. 31:1059-1067).

In further experiments aimed at minimising the number of non-human residues required to retain binding and at optimising biophysical properties (stability and solubility), systematic mutagenesis and domain shuffling was applied allowing to elucidate the functional differences between mouse and humanised VL and VH domains.

Two variants were obtained by domain shuffling. The first variant is composed of the VL domain from TB-A connected via a glycine serine linker (SEQ ID NO:10) with the VH domain from TB-B, resulting in TB-AB (SEQ ID NO:12). The second variant, TB-BA, is the reverse of the first variant, namely, the VL domain from TB-B in combination with the VH domain of TB-A (SEQ ID NO:13).

Additional variants were generated by systematic mutagenesis of TB-A. FIG. 1 shows a sequence comparison of the VL and VH sequences of TB-A and TB-B. A total of 14 framework residues differ between TB-A and TB-B (asterisks). Only five of them, VL residues 4 and 70, and VH residues 28, 71, and 73 show only minor differences in size and property and therefore were not considered for mutagenesis at this point. The following framework positions were replaced with the corresponding amino acid from TB-B. These single or double mutants of TB-A are as follows:

| | | | |
|---|---|---|---|
| TB-A H43 | K→Q | interface | (SEQ ID NO: 18) |
| TB-A H68 | F→V | outer loop VH | (SEQ ID NO: 19) |
| TB-A H70/72 | F→L, L→R | outer loop VH | (SEQ ID NO: 20) |
| TB-A H76/77 | A→I, S→G | outer loop VH | (SEQ ID NO: 21) |
| TB-A L46 | L→R | interface | (SEQ ID NO: 22) |
| TB-A L65 | R→S | outer loop VL | (SEQ ID NO: 23) |
| TB-A L67 | Y→S | outer loop VL | (SEQ ID NO: 24) |

Many factors can influence the immunogenicity of an antibody or antibody derivative (Gonzales et al. (2005), Tumor Biol. 26:31-43). To further reduce the non-human content of the variable regions of the humanised TB-A scFv, the murine CDR2 and CDR3 loops of VL and murine CDR2 loop of VH were exchanged with the corresponding human CDR loops from FW2.3. The resulting constructs herein are referred to as TB_L2 (SEQ ID NO:7), TB_L3 (SEQ ID NO:8), and TB_H2 (SEQ ID NO:9), respectively.

The cDNAs encoding the murine single-chain version of the monoclonal antibody Di62, and the two humanised versions TB-B and TB-A were generated by gene synthesis (www.genscript.com). All the point mutations in the other variants (TB-B L46, TB-A H43, TB-A H67, TB-A H69/71, TB-A H75/76, TB-A L46, TB-A L65, TB-A L67, TB-A V83F, TB-A V83A, TB-A D66G) were introduced by PCR-driven site-directed mutagenesis following standard cloning procedures. Exchange of the murine CDR loops of TB-A with the human CDR loops from FW2.3 was accomplished using PCR and state of the art cloning procedures. The cDNA encoding all the VH TB-A variations as disclosed in SEQ ID NO:28, SEQ ID NO:29, and SEQ ID NO:30 were realized by complete gene synthesis.

Some further preferred TB-A are disclosed in SEQ ID NO: 31 to SEQ ID NO: 38. These antibodies were found to be particularly stable and soluble, as shown below in Table I.

All scFv fragments were cloned into an expression vector for periplasmic production in *E. coli* (Krebber et al. (1997), J. Immunol. Methods 201:35-55).

In addition to the single-chain antibody derivatives (scFvs) described above, the corresponding Fab fragments were generated as follows. Selected light chain variable domains (VL) were fused to the constant region of a human Ig kappa chain, while the suitable heavy chain variable domains (VH) were fused to the first (N-terminal) constant domain (CH1) of a human IgG. Both human constant domains were amplified by PCR from a human spleen cDNA library and resulted in the sequence SEQ ID NO:14 for cκ- and SEQ ID NO:15 for CH1.

Experiment 2

Expression, Production and Stability of Humanised scFv or Fab Antibodies

Plasmids encoding TB-wt, its humanised derivatives, or Fab fragments were introduced into a suitable *E. coli* strain (e.g. JM83) for periplasmic expression. The scFv variants were also expressed as inclusion bodies, for example in the BL21 *E. coli* strain. Functional single-chain antibodies were obtained by refolding of inclusion bodies and subsequent purification by, for example, gel filtration.

The expression yields upon periplasmic expression of the scFvs ranged between 0.5 mg up to 12 mg per liter culture under standard laboratory cultivation conditions (dYT medium, with approx. 3 hours induction time at 30° C., shaking at 200 rpm) with conventional shaking flasks. In general, we observed that, as expected from our previous analysis of frameworks selected for stability and solubility (Auf der Maur, et al. (2004), Methods 34:215-224), the closer the sequence of a humanised derivative is to the sequence of the acceptor framework (FW2.3), the higher is the yield obtained upon expression in bacteria. For example, the yield obtained from expression of TB-B is far better than that obtained from expression of TB-A. In accordance with these findings, reducing the number of differing amino acid residues present in TB-A had a positive effect toward the expression yields (FIG. 3A).

Another important characteristic of the antibodies or antibody derivatives of the present invention is their solubility. FIG. 3B shows the superiority of the framework TB-A over the donor framework (TB-wt) in terms of solubility in phosphate buffered saline. In analytical gel filtration, TB-A migrates predominantly in a monomer state (peak at 70 ml) whereas TB-wt shows a strong tendency to form aggregates (peak at 50 ml). In addition to that, maximal solubility of TB-A and certain derivatives thereof was assessed by PEG precipitation (Athat D H. et al. JBC. 1981, 256; 23. 12108-12117). Briefly, the apparent solubility of test proteins was measured in the presence of polyethylene glycol 3000 (PEG3000). Solubility curves were determined by measuring protein concentration in the supernatant of centrifuged protein-PEG300 mixtures. All curves showed a linear dependence of log S (mg/ml) on PEG3000 concentration (%, w/v). Maximal solubility ($S_{max}$) of a test protein was estimated by extrapolation of the linear regression towards 0% PEG (Tab. I). For TB-A was $S_{max}$ calculated to be about 70 mg/ml. All test proteins showed exceptionally good solubility. In a second approach a method called self-interaction chromatography (SIC) was applied to assess intermolecular attraction/repulsion of TB-A (SEQ ID NO:40), TB-A Linker_G2R H_F68L (SEQ ID NO:33), TB-A H_K43R/F68I (SEQ ID NO:34) and TB-A H_F68L (SEQ ID NO:35) at a concentration of 1 mg/ml in PBS (50 mM phosphate pH 6.5, 150 mM NaCl). In this method the protein of interest is immobilized onto a porous stationary phase and packed into a column. Interactions between the free (mobile phase) and immobilized protein are detected as shifts in the retention volume. The protein osmotic second virion coefficient $B_{22}$, which is a measure for intermolecular attraction/repulsion, was calculated according to Tessier, P M et al. Biophys. J. 2002, 82: 1620-1632 (Tab. I). The more positive $B_{22}$, the lower is the intermolecular attraction of the test protein and, therefore, the higher is its solubility. Due to the high similarity of test protein sequences it was assumed that $B_{22}$ values of the different proteins can be directly compared to each other.

TABLE I

Solubility features of TB-A derivatives

| Sequence | pI | Log $S_{max}$ | $B_{22}$ value (SIC) |
|---|---|---|---|
| TB-A | 7.8 | 1.84 ± 0.13 | $-24.5 \times 10^{-4} \pm 3.8 \times 10^{-4}$ |
| TB-A H_M48L/F68I | 7.8 | nd | nd |
| TB-A L_V83E H_V79A | 6.58 | nd | nd |
| TB-A Linker_G2R H_F68L | 8.2 | 1.91 ± 0.09 | $1.59 \times 10^{-3} \pm 5.9 \times 10^{-5}$ |
| TB-A H_K43R/F68I | 7.8 | 1.86 ± 0.02 | $1.28 \times 10^{-3} \pm 3.0 \times 10^{-4}$ |
| TB-A H_F68L | 7.8 | 1.88 ± 0.07 | $1.06 \times 10^{-4} \pm 2.9 \times 10^{-5}$ |
| TB-A H_F68A | 7.8 | nd | nd |
| TB-A H_F68V/F70L | 7.8 | nd | nd |
| TB-A H_F70L | 7.8 | nd | nd |

Yet another relevant feature of the antibodies or antibody derivatives of the present invention is their high stability. Protein stability of TB-A, TB-A H_M48L/F68I (SEQ ID NO: 31), TB-A Linker_G2R H_F68L (SEQ ID NO:33), TB-A H_K43R/F68I (SEQ ID NO:34) and TB-A H_F68L (SEQ ID NO:35) was assessed by determining the temperature for onset of unfolding by circular dichroism and light scattering at both 218 and 292 nm (Tab. II). In this experiment TB-A started to unfold at a temperature of 53° C. whereas its derivatives TB-A H_M48L/F68I (SEQ ID NO:31), TB-A Linker_G2R H_F68L (SEQ ID NO:33), TB-A H_K43R/F68I (SEQ ID NO:34) and TB-A H_F68L (SEQ ID NO:35) showed increased thermal stability (56 and 58° C.). All test proteins showed irreversible denaturation and precipitated upon unfolding, making it impossible to determine the melting temperature. In order to determine midpoint of transition in a reversible process, unfolding was induced with guanidine hydrochloride (GdnHCl), to keep the unfolded proteins in solution. In this approach fluorescence emission maxima where determined in by fluorimetry to follow unfolding. In this set-up, TB-A showed again good stability with a midpoint of transition at 2.07 M GdnHCl. In line with the results from thermal unfolding the derivatives TB-A Linker_G2R H_F68L (SEQ ID NO:33) and TB-A H_K43R/F68I (SEQ ID NO:34) showed increased stability as displayed with higher midpoints of transition, 2.33 and 2.3 M GdnHCl, respectively.

TABLE II

Stability features of TB-A derivatives

| SEQ | Onset of denaturation [° C.] | [GdnHCl] at midpoint of transition |
|---|---|---|
| TB-A | 53 | 2.07M |
| TB-A H_M48L/F68I | 58 | nd |
| TB-A L_V83E H_V79A | nd | nd |
| TB-A Linker_G2R H_F68L | 58 | 2.33M |
| TB-A-QC15.2 | 56 | 2.30M |
| TB-A-QC23.2 | 58 | nd |
| TB-A-H_F68A | nd | nd |
| TB-A H_F68V/F70L | nd | nd |
| TB-A H_F70L | nd | nd |

Figure 11:
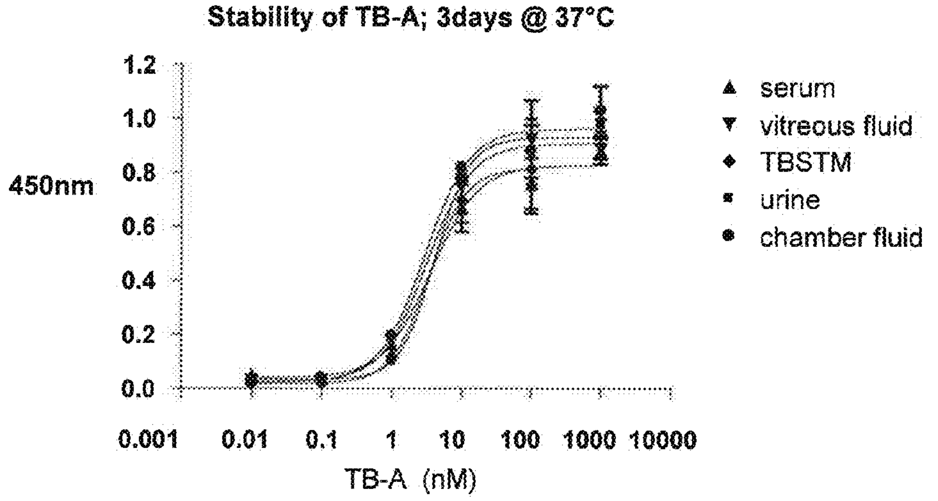
FIG. 11 shows the stability of TB-A in different body fluids.

The stability of TB-A in human serum, human urine, pig vitreous body fluid and pig anterior chamber fluid was assayed by measuring TNFα binding activity of TB-A after incubation for 3 days at 37° C. in the respective body fluid or in assay buffer (TBSTM) as a positive control. TB-A was diluted in body fluids to a final concentration of 10 μM. After the incubation period dilution series of the samples were assayed by ELISA in order to determine the binding constant $K_d$ of TB-A (FIG. 11). When comparing body fluid samples with the positive control TBSTM samples, a shift of the $K_d$ towards higher concentrations would indicate a decrease of active protein during the incubation period. In our experiments, however, no such shift was detectable, indicating that the amount of fully active TB-A remained constant in every body fluid assay due to a high stability of the antibody.

Experiment 3

Binding Features of Humanised Antibody Derivatives

The binding properties of all humanised scFv variants were tested in ELISA on recombinant human TNFα. The dissociation constants ($K_d$) for all variants lay within a range of 0.8 to more than 10,000 nM. There seems to exist a reverse correlation between the grade of homology to the human acceptor framework and the affinity of the respective binder (FIG. 4A). Nevertheless, some TB-A variants containing mutations towards the TB-B sequence show affinity levels towards human TNFα that are comparable to that of TB-A. FIG. 4B shows two expression yield-improved derivatives of TB-A (compare FIG. 3A) that exhibit similar affinities as TB-A when compared in ELISA.

TB-A represents a good compromise between the apparent trade-off of expression yield and affinity. In terms of affinity, no significant difference between the single-chain and the Fab fragment format of TB-A was detectable (data not shown).

The affinity for TNFα and binding kinetics were also determined for TB-A by surface plasmon resonance (BIACore), resulting in a dissociation constant $K_d$=0.8 nM, an off rate of $k_{off}$=$4.4\times10^{-4}$ $s^{-1}$ and a on rate of $k_{on}$=$5\times10^{5}$ $s^{-1}$ $m^{-1}$.

Experiment 4

L929 Cytotoxicity Assay

Figure 5:
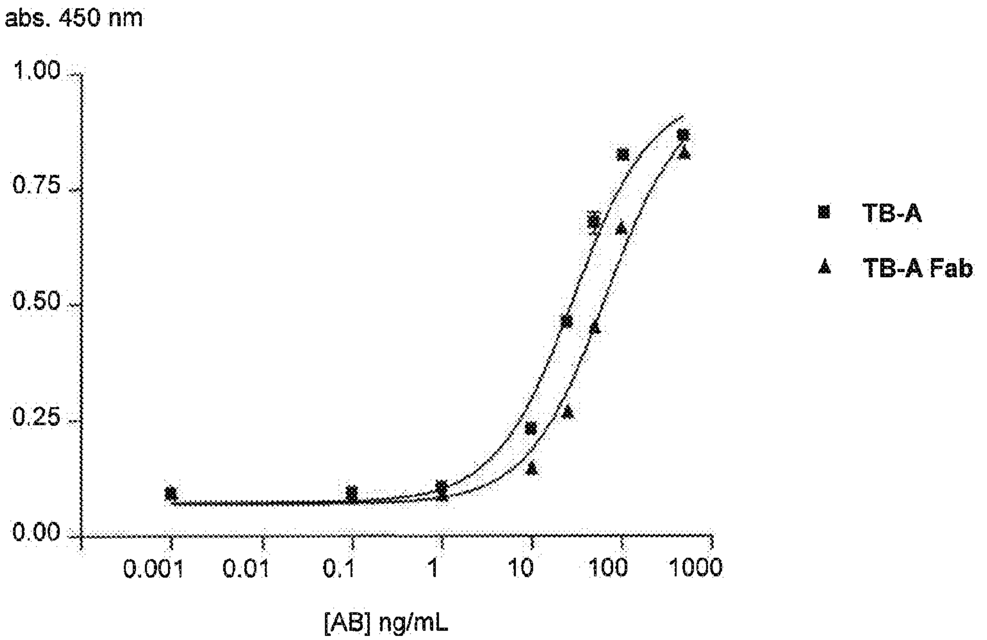
FIG. 5 shows the inhibition of human TNFα-induced cytotoxicity in mouse L929 fibroblasts. A. Concentration dependent inhibition of TB-A in comparison to TB-wt and infliximab with $IC_{50}$ values. B. Comparison of TB-A derivatives to block TNFα induced cytotoxicity. C. Comparison of scFv and Fab formats of TB-A.

The function of antibodies or antibody derivatives in neutralising TNFα in vivo can be tested by measuring inhibition of cytotoxicity of TNFα towards cultured mouse L929 fibroblasts or alternatively towards human KYM-1 myelosarcoma cells (Tab. III). The humanised scFv derivatives of Di62 display different efficacies in the L929 assay as shown in FIG. 5B. Some scFv derivatives show IC50 (inhibitory concentration to achieve 50% inhibition) values in the range of 5 ng/ml, whereas others had no effect in the L929 assays. ELISA data and results from the L929 assay do not always correlate. KYM-1 data and L929 results, however, correlated nicely with the only difference that much higher concentrations of recombinant human TNF and consequently also of the antagonist where required to see an effect. KYM-1 was, therefore, mainly used to confirm L929 results. For direct comparison of test proteins, potency is expressed as a relative value normalized to TB-A ($EC_{50}X/EC_{50}TB\text{-}A$). In general, however, IC50 values become again higher the closer the sequence of a binder is to the human acceptor framework (FW2.3). FIG. 5 compares the potency of different derivatives of TB-A to block TNFα induced cytotoxicity towards mouse L929 fibroblast cells. Absorption at 450 nm correlates with cell survival.

TB-A and the anti-hTNFα IgG Infliximab® show a similar $IC_{50}$ value in the L929 assay, whereas the potency of TB-wt to block human TNFα induced cytotoxicity is significantly lower (FIG. 5A). When TB-A derivatives are compared with TB-A for their potential to block TNFα induced cytotoxicity, most of these derivatives except TB-H43 have a reduced efficacy in the L929 (FIG. 5B).

TABLE III

Functional properties of TB-A derivatives

| | Relative potency: $EC_{50}X/EC_{50}TB\text{-}A$ | |
|---|---|---|
| SEQ | L929 cells | KYM-1 cells |
| TB-A | 1.0 | 1.0 |
| TB-A H_M48L/F68I | 1.1 | 1.6 |
| TB-A L_V83E H_V79A | Nd | nd |
| TB-A Linker_G2R H_F68L | 0.8 | 1.3 |
| TB-A-QC15.2 | 1.37 | 1.5 |
| TB-A-QC23.2 | 1.32 | 1.5 |
| TB-A-H_F68A | 1.14 | nd |
| TB-A H_F68V/F70L | 1.28 | nd |
| TB-A H_F70L | 2.7 | nd |

In line with the ELISA data, there is no significant difference in the ability to block TNFα-induced cytotoxicity between the scFv and the Fab format of TB-A (FIG. 5C). The $IC_{50}$ value of the TB-A Fab format lies about a factor of two above the $IC_{50}$ value of the TB-A scFv format (FIG. 5C), most probably as a result of the higher molecular mass of the Fab fragment.

Experiment 5

Animal Experiments with Anti-TNFα Antibody Derivatives

5.1. Description of Experiment

In order to test for the efficacy of ESBATech's anti-TNFα antibody derivatives (scFv and Fab) in functionally neutralising human TNFα bioactivity in an in vivo situation, a recently published rat model for acute monoarthritis was used. This model has extensively been described by Bolon and colleagues (see Bolon et al. (2004), Vet. Pathol. 41:235-243). Briefly, in this animal arthritis model, human TNFα is injected intra-articularly into the knee joint of male Lewis rats. Injection of human TNFα leads to an acute, self-limiting monoarthritis in the injected joint. Arthritis can be quantified by measurement of joint swelling and histological scoring. Consequently, bioactivity of respective TNFα antagonists can be quantified by reduction of TNFα-induced joint swelling and/or reduction of histological parameters of inflammation.

5.2. Materials and Methods

Experimental Design

The current studies were designed to examine the respective potential of a representative scFv antibody and a representative Fab antibody of the series described above with the marketed antibody Infliximab (Remicade®) to inhibit bioactivity of human TNFα in an appropriate animal arthritis model. Bolon and colleagues had shown before that intraarticular application of 10 microgram of recombinant human TNFα into the rat knee joint provokes an acute, self-limiting monoarthritis that can be quantified by standard macroscopic and microscopic analysis. Thus this animal model served as ideal system to assess the therapeutic effect of locally applied antibody derivatives. Two experiments were completed in series (Tab. IV and V). 1) A basic efficacy study assessing the overall potential of the antibodies to block human TNFα-induced monoarthritis; and 2) A dose response study assessing the relative efficacy of the antibody derivatives among each other. Both, cytokines and antibody derivatives were given once by separate injections, as described below. The cytokine dose used was based on the publication by Bolon and colleagues, whereas the range of doses of the antibody derivatives was based on available cell culture data and educated guessing. The experiments were conducted in accordance with general animal care guidelines.

Animals and Husbandry

Young, adult male Lewis rats (6-7 weeks and 175-200 g) were randomly assigned to treatment groups (n=3/cohort) and housed according to Bolon et al. (2004), Vet. Pathol. 41:235-243.

Cytokine and Antibody Instillation

Anaesthesia and cytokine injections were performed as described by Bolon and colleagues. In order not to exceed a total intraarticularly injected volume of 50 microliter, cytokines and antibody derivatives were instilled in two separate intra-articular injections whereby the 10 micrograms of recombinant human TNFα was injected in 10 microliter of filter-sterilised phosphate-buffered saline (PBS) and the respective dose of the respective antibody was injected in 40 microliter of filter-sterilised phosphate-buffered saline. Animals treated with intraperitoneally applied Infliximab/Remicade® were i.p. injected with the antibody derivatives 3 hours prior to intra articular injection of the human TNFα. In all animals treated with intraarticularly applied antibody treatments, the respective antibody dose was injected 5 minutes prior to injection of the human TNFα. Control animals were injected with 10 microliter of PBS without human TNFα.

Infliximab/Remicade® used in the experiments was purchased at an official Swiss pharmacy. Anti-human TNFα specific scFv and Fab (TB-A) antibodies as well as a naïve scFv antibody framework used as unspecific control antibody in the dose response experiment were expressed in *E. coli* and purified by standard methods. Endotoxin contamination was held below 10 EU per milligram protein in all preparations because the lipopolysaccharide component is a potent inducer of TNFα.

Recombinant human TNFα was purchased from PeproTech EC Ltd.

Measurement of Joint Diameter

Figure 6:
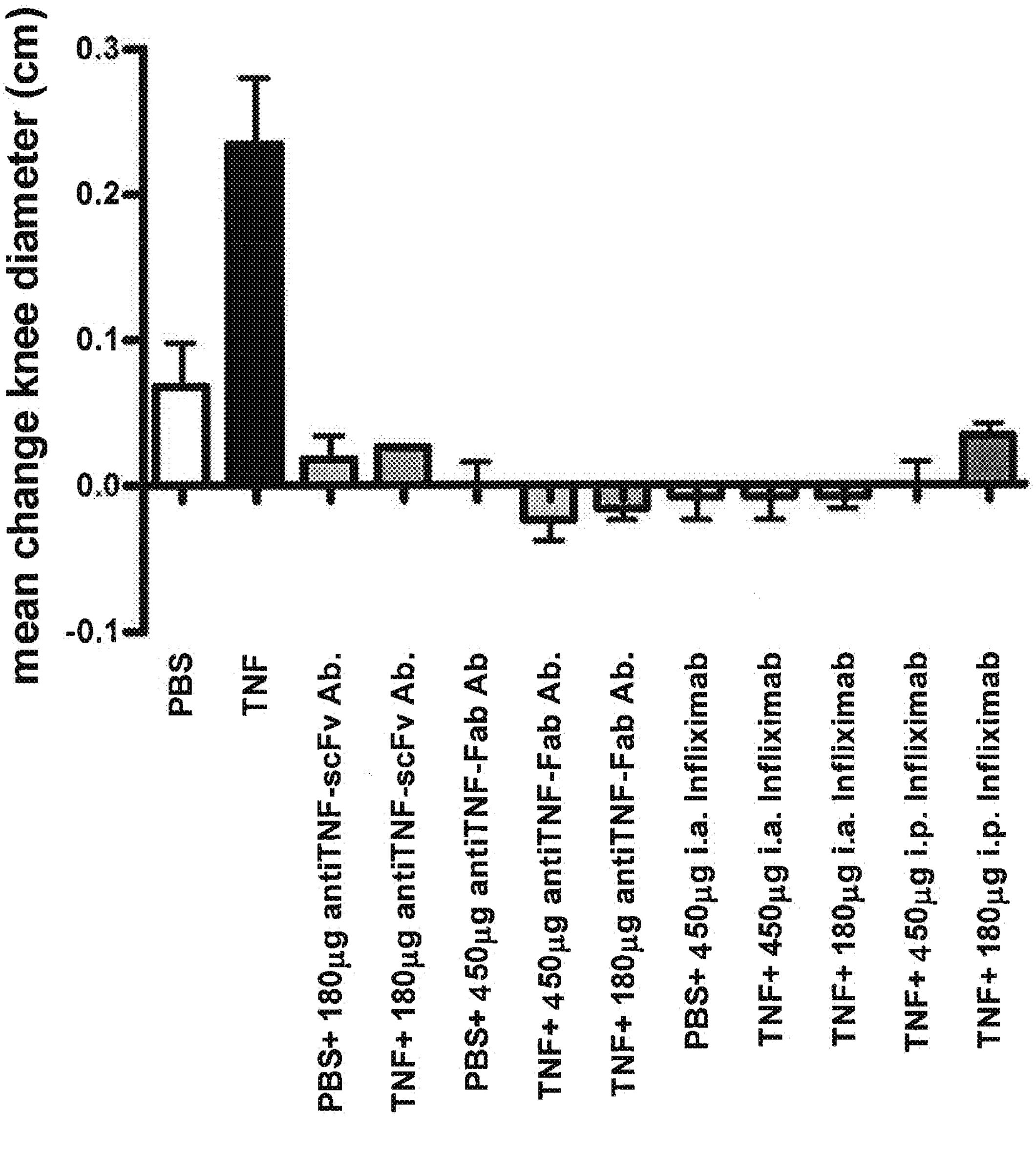
FIG. 6 shows the effect of antibody treatment of human TNFα-induced joint swelling in rat (Experiment: 5.3, Experiment 1).
Figure 9:
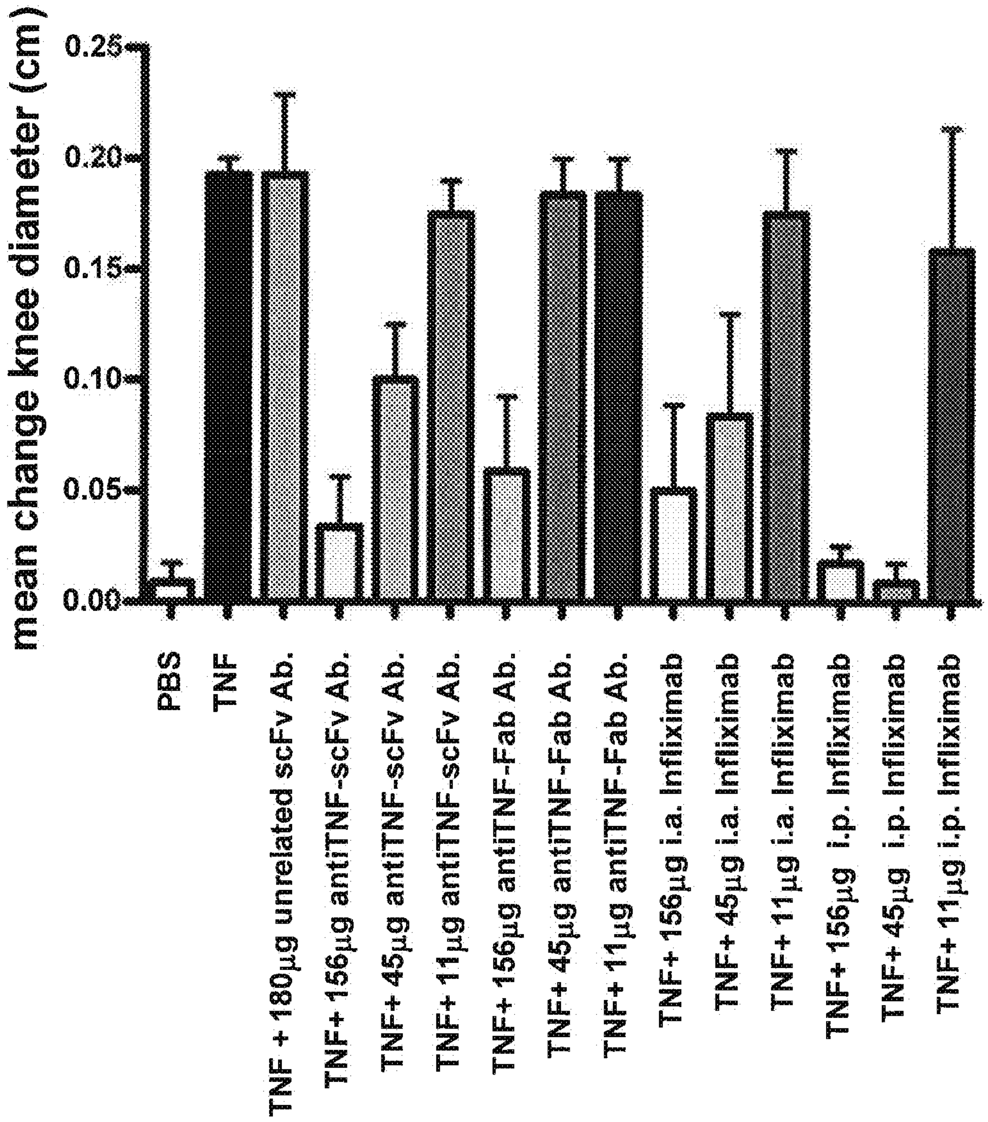
FIG. 9 shows the effect of antibody treatment of human TNFα-induced joint swelling in rat (Experiment: 5.3, Experiment 2).

Immediately before the injection of the respective, intraperitoneally or intraarticularly applied antibody derivative, or, in case of the control animals, before the injection of PBS or TNFα, the diameter of the knee joint to be injected was determined by means of a standard caliper. 48 hours after injection of TNFα (or PBS in control animals) and immediately before euthanisation of the animals, the diameter of the injected knee joint was determined again and joint swelling was calculated by subtracting the value of the second diameter measurement from the value of the first diameter measurement (FIGS. 6 and 9).

Tissue Processing 48 hours after injection of TNFα (or PBS in case of control animals) animals were euthanised. At necropsy, injected knees were separated from the foot and thigh, fixed intact by immersion in 70% ethanol and proceeded for standard hematoxylin and eosin (HE) staining, as described by Bolon and colleagues.

Morphologic Analysis

Figure 7:
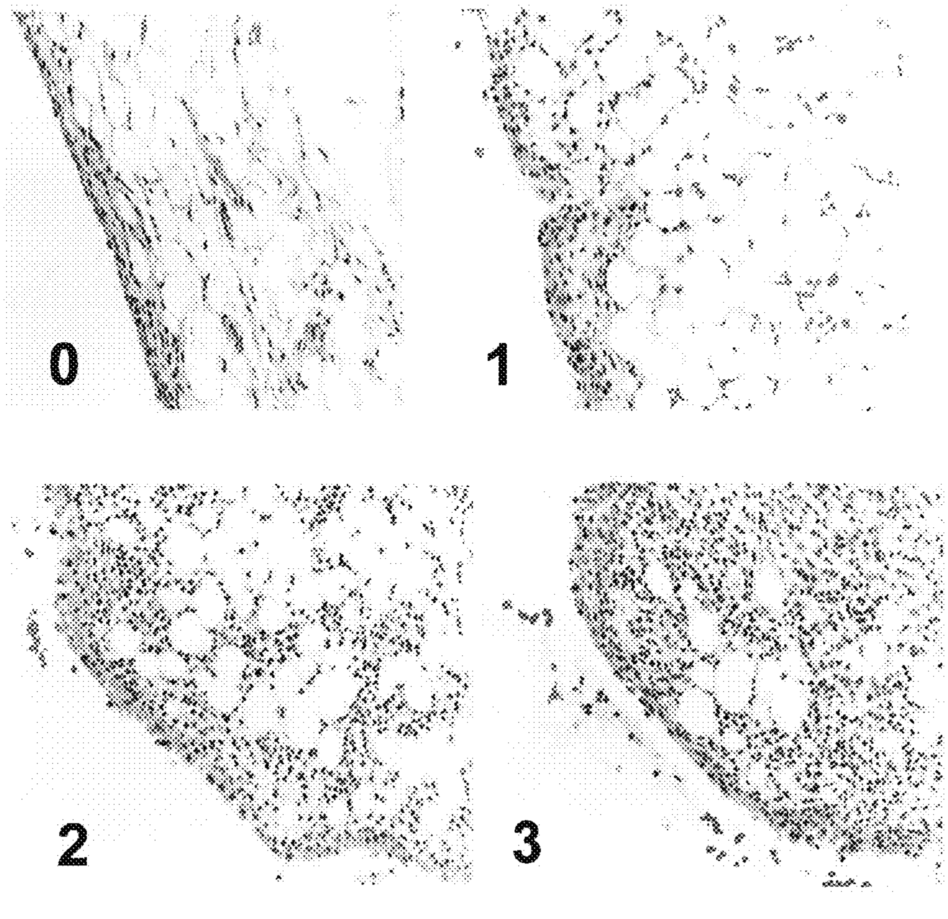
FIG. 7 shows the scoring scheme for histopathological inflammation scoring.
Figure 8:
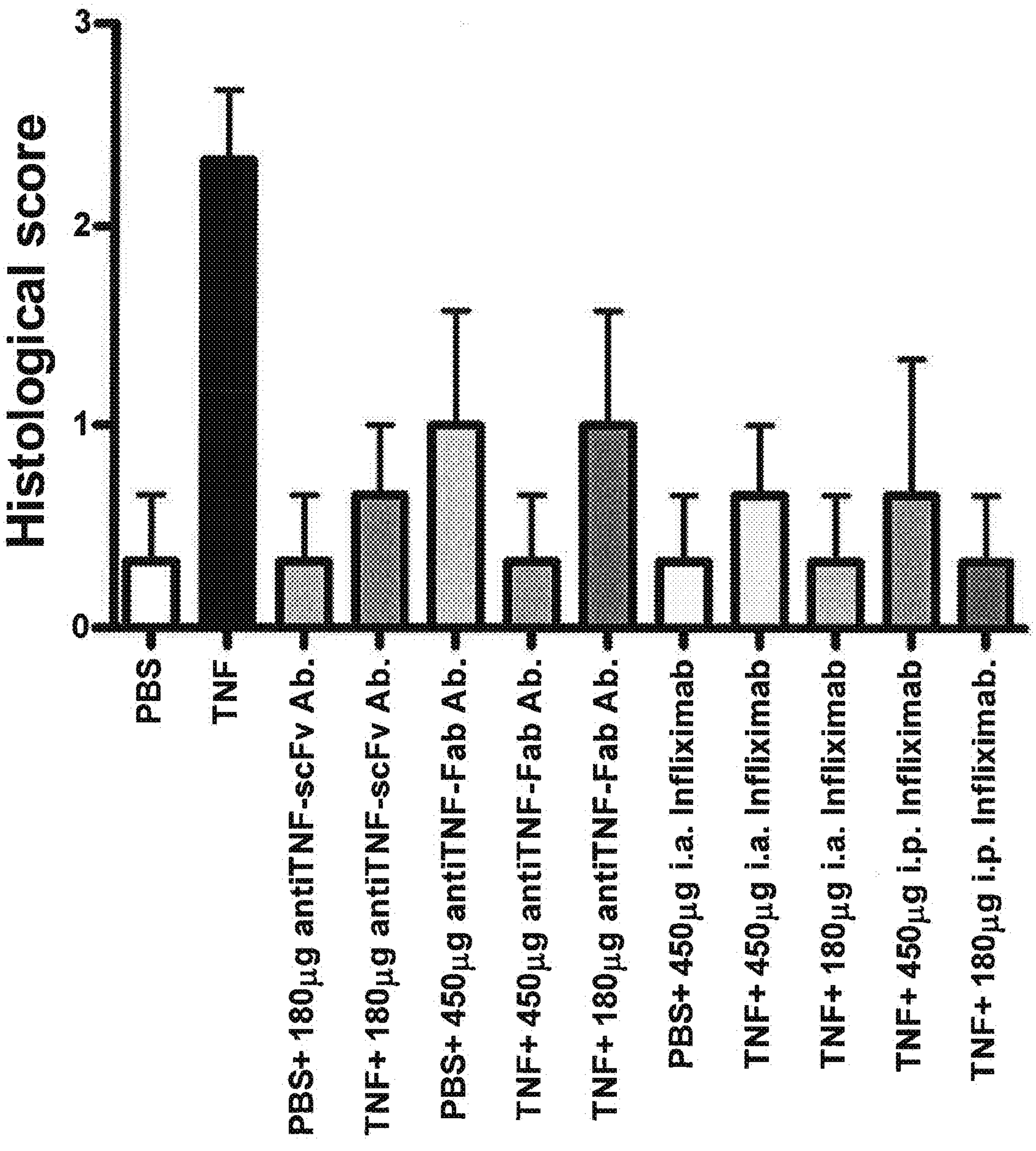
FIG. 8 shows the effect of antibody treatment on human TNFα-induced joint inflammation in rat (Experiment: 5.3, Experiment 1).
Figure 10:
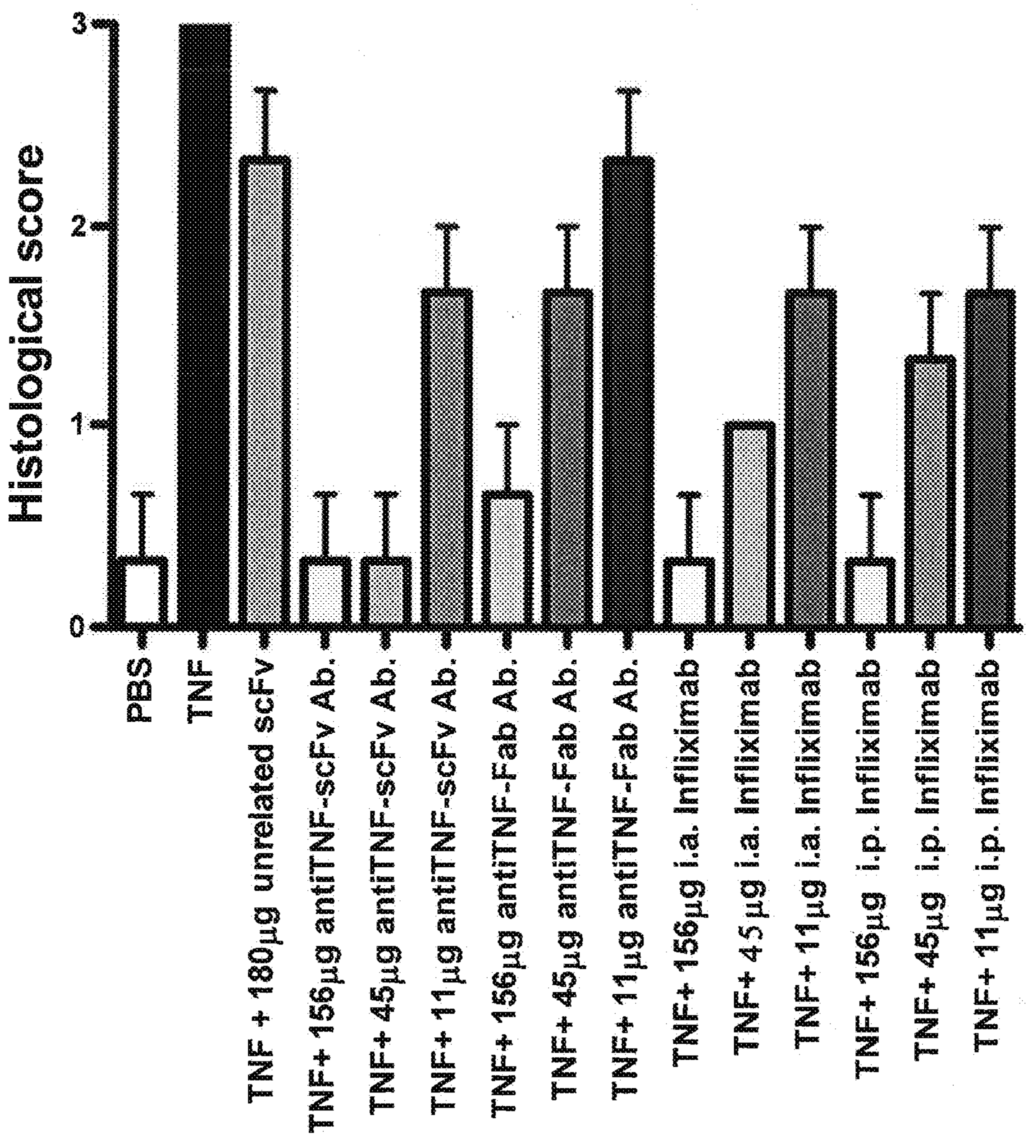
FIG. 10 shows the effect of antibody treatment on human TNFα-induced joint inflammation in rat (Experiment: 5.3, Experiment 2).

Histological scoring analysis for measurement of joint inflammation was performed as described by Bolon and colleagues. Histopathological scoring criteria for assessment of joint inflammation were applied according to Bolon and colleagues (FIGS. 7, 8 and 10).

5.3. Results

In a first set of experiments a representative intraarticularly applied ESBATech scFv antibody, TB-A, and the corresponding intraarticularly applied ESBATech Fab antibody were compared for their ability to block induction of the acute monoarthritis with intraarticularly and intraperitoneally applied Infliximab/Remicade® according to Table IV:

TABLE IV

Injection scheme experiment 1

| GROUP | TNFα (μg) in PBS | INHIBITOR | DOSE (μg) |
|---|---|---|---|
| 1 (n = 3) | 0 | none | |
| 2 (n = 3) | 10 | none | |
| 3 (n = 3) | 0 | TB-A scFv | 180 |
| 4 (n = 3) | 10 | TB-A scFv | 180 |
| 5 (n = 3) | 0 | TB-A Fab antibody | 450 |
| 6 (n = 3) | 10 | TB-A Fab antibody | 450 |
| 7 (n = 3) | 10 | TB-A Fab antibody | 180 |
| 8 (n = 3) | 0 | Infliximab (i.a.) | 450 |
| 9 (n = 3) | 10 | Infliximab (i.a.) | 450 |
| 10 (n = 3) | 10 | Infliximab (i.a.) | 180 |
| 11 (n = 3) | 10 | Infliximab (i.p.) | 450 |
| 12 (n = 3) | 10 | Infliximab (i.p.) | 180 |

The results obtained regarding treatment effects on change of knee diameter (as an indicator of effects on TNFα-induced joint swelling) are represented in FIG. 6. All antibodies completely blocked TNFα-induced joint swelling.

For evaluation of treatment effects on joint inflammation, histological scoring of HE-stained tissue slides was performed. Joint inflammation was scored by the following criteria (see FIG. 7 for representative scoring examples):

Score 0: normal

Score 1: Mild thickening of synovial lining

Score 2: Thickening of synovial lining and mild inflammation of the sublining

Score 3: Thickening of synovial lining and moderate inflammation of the sublining The results obtained regarding treatment effects on histopathological inflammation scores are shown in FIG. 8.

Comparable effects of all treatment on histopathological inflammation scores were observed.

In a second set of experiments, the relative dose response to the assessed antibody derivatives was compared. The representative intraarticularly applied ESBATech scFv antibody TB-A and the corresponding intraarticularly applied Fab antibody of experiment 1 were compared with intraarticularly and intraperitoneally applied Infliximab/Remicade® and an unrelated scFv antibody lacking any binding activity to human TNFα over a broader and different dose range as compared with experiment 1, according to Table V.

TABLE V

Injection scheme experiment 2

| GROUP | TNFα (μg) in PBS | INHIBITOR | DOSE (μg) |
|---|---|---|---|
| 1 (n = 3) | 0 | none | |
| 2 (n = 3) | 10 | none | |
| 3 (n = 3) | 10 | Unrelated scFv antibody | 180 |
| 4 (n = 3) | 10 | TB-A scFv antibody | 156 |
| 5 (n = 3) | 10 | TB-A scFv antibody | 45 |
| 6 (n = 3) | 10 | TB-A scFv antibody | 11 |
| 7 (n = 3) | 10 | TB-A Fab antibody | 156 |
| 8 (n = 3) | 10 | TB-A Fab antibody | 45 |
| 9 (n = 3) | 10 | TB-A Fab antibody | 11 |
| 10 (n = 3) | 10 | Infliximab (i.a.) | 156 |
| 11 (n = 3) | 10 | Infliximab (i.a.) | 45 |
| 12 (n = 3) | 10 | Infliximab (i.a.) | 11 |
| 13 (n = 3) | 10 | Infliximab (i.p.) | 156 |
| 14 (n = 3) | 10 | Infliximab (i.p.) | 45 |
| 15 (n = 3) | 10 | Infliximab (i.p.) | 11 |

The results obtained regarding treatment effects on change of knee diameter (as an indicator of effects on TNFα-induced joint swelling) are shown in FIG. 9.

The results obtained regarding treatment effects on histopathological inflammation scores are presented in FIG. 10.

In summary, both the representative ESBATech anti-TNFα scFv and the representative ESBATech anti-TNFα Fab antibody were highly efficient in blocking human TNFα-induced monoarthritis upon local (intraarticular) administration.

While there are shown and described presently preferred embodiments of the invention, it is to be distinctly understood that the invention is not limited thereto but may be otherwise variously embodied and practiced within the scope of the following claims.

The invention claimed is:

1. A method for inhibiting TNFα comprising administering to a patient in need thereof a stable and soluble antibody which specifically binds TNFα, said antibody comprising a light chain variable domain (VL) comprising the sequence of SEQ ID NO:1 and a heavy chain variable domain (VH) comprising the sequence of SEQ ID NO:2, or an antigen-binding derivative thereof, wherein said derivative has at maximum up to five amino acid changes as compared to SEQ ID NO: 1 and/or at maximum up to nine amino acid changes as compared to SEQ ID NO: 2, wherein said changes occur at amino acid positions in framework regions of said VL comprising the sequence of SEQ ID NO: 1 and said VH comprising the sequence of SEQ ID NO: 2, and wherein said derivative does not comprise the entire sequences of SEQ ID NO: 3 and SEQ ID NO: 4.

2. The method of claim 1, wherein the antibody or antigen-binding derivative is locally or topically administered.

3. The method of claim 1, wherein the patient has a disease selected from the group consisting of: osteoarthritis, uveitis, dry eye, inflammatory bowel disease, Behcet's disease, Crohn's disease, psoriasis and pyoderma gangraenosum.

4. The method of claim 1, wherein the up to 5 changes of VL are at any of the positions 4, 46, 65, 67, 70, and 83 and the up to 9 changes of VH are at any of the positions 11, 16, 28, 43, 68, 70, 71, 72, 73, 76, 77, 93 and 112.

5. The method of claim 1, wherein the up to 5 changes of VL are at any of the positions 4, 46, 65, 67, 70, and 83 and the up to 9 changes of VH are at any of the positions 11, 16, 28, 43, 48, 68, 70, 71, 72, 73, 76, 77, 79, 93 and 112.

6. The method of claim 1, in which at least one of the changes leads to an amino acid present in SEQ ID NO:3 at a corresponding position in SEQ ID NO: 1 for VL and/or leads to an amino acid present in SEQ ID NO:4 at a corresponding position in SEQ ID NO: 2 for VH, wherein said derivative does not comprise the entire sequences of SEQ ID NO: 3 and SEQ ID NO: 4.

7. The method of claim 1, wherein the VL domain of the antibody or antigen-binding derivative comprises the sequence of SEQ ID NO: 1.

8. The method of claim 7, wherein the antibody or antigen-binding derivative comprising the VH domain of the sequence of SEQ ID NO: 2.

9. The method of claim 8, wherein the antibody or antigen-binding derivative comprising a VH domain derived from the sequence of SEQ ID NO:2, wherein F68 is changed to A, L, I, or V.

10. The method of claim 1, wherein the antibody or antigen-binding derivative comprises the VL domain of the sequence of SEQ ID NO: 11, and the VH domain of the sequence of SEQ ID NO: 4.

11. The method of claim 1, wherein the antibody or antigen-binding derivative is an scFv antibody wherein the VL and VH domains are connected by a linker.

12. The method of claim 11, wherein the scFv antibody comprises a VL-linker-VH sequence arrangement.

13. The method of claim 11, wherein the linker has the sequence of SEQ ID NO:10 or is derived from said sequence.

14. The method of claim 13, wherein at least one G of said linker is changed to a more polar or charged amino acid.

15. The method of claim 1, wherein the antibody or antigen-binding derivative is a Fab fragment wherein the VL domain is fused to the constant region of a human Ig kappa chain, the VH domain is fused to the CH1 domain of a human IgG, and the two fusion polypeptides are connected by an inter-chain disulfide bridge.

16. The method of claim 1, wherein the antibody comprises a light chain variable domain (VL) comprising the sequence of SEQ ID NO: 1 and a heavy chain variable domain (VH) comprising the sequence of SEQ ID NO: 2 and a linker derived from the sequence of SEQ ID NO: 10.

17. The method of claim 16, wherein at least one G of SEQ ID NO: 10 is changed to a more polar or charged amino acid.

18. The method of claim 16, which is an scFv antibody.

19. The method of claim 16, wherein the antibody is locally or topically administered.

20. The method of claim 16, wherein the antibody is administered to a patient that has osteoarthritis, uveitis, dry eye, inflammatory bowel disease, Behcet's disease, Crohn's disease, psoriasis or pyoderma gangraenosum.

* * * * *

SEQUENCE LISTING

<160> NUMBER OF SEQ ID NOS: 41

<210> SEQ ID NO 1
<211> LENGTH: 108
<212> TYPE: PRT
<213> ORGANISM: artificial
<220> FEATURE:
<223> OTHER INFORMATION: derivative of TB-B

<400> SEQUENCE: 1

```
Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg
            100                 105


<210> SEQ ID NO 2
<211> LENGTH: 117
<212> TYPE: PRT
<213> ORGANISM: artificial
<220> FEATURE:
<223> OTHER INFORMATION: derivative of TB-B

<400> SEQUENCE: 2

Gln Val Gln Leu Val Gln Ser Gly Ala Glu Val Lys Lys Pro Gly Ala
1               5                   10                  15

Ser Val Lys Val Ser Cys Thr Ala Ser Gly Tyr Thr Phe Thr His Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Pro Thr Tyr Ala Asp Lys Phe
    50                  55                  60

Lys Asp Arg Phe Thr Phe Ser Leu Glu Thr Ser Ala Ser Thr Val Tyr
65                  70                  75                  80

Met Glu Leu Thr Ser Leu Thr Ser Asp Asp Thr Ala Val Tyr Tyr Cys
                85                  90                  95

Ala Arg Glu Arg Gly Asp Ala Met Asp Tyr Trp Gly Gln Gly Thr Leu
            100                 105                 110

Val Thr Val Ser Ser
        115


<210> SEQ ID NO 3
<211> LENGTH: 108
<212> TYPE: PRT
<213> ORGANISM: Artificial
<220> FEATURE:
<223> OTHER INFORMATION: VL/TB-B

<400> SEQUENCE: 3

Asp Ile Val Leu Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Arg Leu Ile
        35                  40                  45

Tyr Ser Ala Phe Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg
            100                 105


<210> SEQ ID NO 4
<211> LENGTH: 117
<212> TYPE: PRT
<213> ORGANISM: Artificial
<220> FEATURE:
<223> OTHER INFORMATION: VH/TB-B

<400> SEQUENCE: 4

Gln Val Gln Leu Val Gln Ser Gly Ala Glu Val Lys Lys Pro Gly Ala
1               5                   10                  15

Ser Val Lys Val Ser Cys Thr Ala Ser Gly Tyr Ser Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Lys Asp Arg Val Thr Leu Thr Arg Asp Thr Ser Ile Gly Thr Val Tyr
65                  70                  75                  80

Met Glu Leu Thr Ser Leu Thr Ser Asp Asp Thr Ala Val Tyr Tyr Cys
                85                  90                  95

Ala Arg Glu Arg Gly Asp Ala Met Asp Tyr Trp Gly Gln Gly Thr Leu
            100                 105                 110

Val Thr Val Ser Ser
        115


<210> SEQ ID NO 5
<211> LENGTH: 108
<212> TYPE: PRT
<213> ORGANISM: human

<400> SEQUENCE: 5

Asp Ile Val Leu Thr Gln Ser Pro Ser Ser Leu Ser Ala Ser Val Gly
1               5                   10                  15

Asp Arg Val Thr Leu Thr Cys Arg Ala Ser Gln Gly Ile Arg Asn Glu
            20                  25                  30

Leu Ala Trp Tyr Gln Gln Arg Pro Gly Lys Ala Pro Lys Arg Leu Ile
        35                  40                  45

Tyr Ala Gly Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Val Tyr Tyr Cys Gln Gln Tyr Tyr Ser Leu Pro Tyr
                85                  90                  95

Met Phe Gly Gln Gly Thr Lys Leu Glu Val Lys Arg
            100                 105


<210> SEQ ID NO 6
<211> LENGTH: 124
<212> TYPE: PRT
<213> ORGANISM: human

<400> SEQUENCE: 6

Gln Val Gln Leu Val Gln Ser Gly Ala Glu Val Lys Lys Pro Gly Ala
1               5                   10                  15
```

```
Ser Val Lys Val Ser Cys Thr Ala Ser Gly Tyr Ser Phe Thr Gly Tyr
            20                  25                  30

Phe Leu His Trp Val Arg Gln Ala Pro Gly Gln Gly Leu Glu Trp Met
        35                  40                  45

Gly Arg Ile Asn Pro Asp Ser Gly Asp Thr Ile Tyr Ala Gln Lys Phe
    50                  55                  60

Gln Asp Arg Val Thr Leu Thr Arg Asp Thr Ser Ile Gly Thr Val Tyr
65                  70                  75                  80

Met Glu Leu Thr Ser Leu Thr Ser Asp Asp Thr Ala Val Tyr Tyr Cys
                85                  90                  95

Ala Arg Val Pro Arg Gly Thr Tyr Leu Asp Pro Trp Asp Tyr Phe Asp
            100                 105                 110

Tyr Trp Gly Gln Gly Thr Leu Val Thr Val Ser Ser
        115                 120


<210> SEQ ID NO 7
<211> LENGTH: 108
<212> TYPE: PRT
<213> ORGANISM: artificial
<220> FEATURE:
<223> OTHER INFORMATION: derivative of TB-A

<400> SEQUENCE: 7

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ala Gly Ser Ile Leu Gln Ser Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg
            100                 105


<210> SEQ ID NO 8
<211> LENGTH: 108
<212> TYPE: PRT
<213> ORGANISM: artificial
<220> FEATURE:
<223> OTHER INFORMATION: derived from TB-A

<400> SEQUENCE: 8

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Tyr Tyr Ser Leu Pro Tyr
                85                  90                  95
```

Met Phe Gly Gln Gly Thr Lys Leu Glu Val Lys Arg
100 105

<210> SEQ ID NO 9
<211> LENGTH: 117
<212> TYPE: PRT
<213> ORGANISM: artificial
<220> FEATURE:
<223> OTHER INFORMATION: derivative of TB-A

<400> SEQUENCE: 9

Gln Val Gln Leu Val Gln Ser Gly Ala Glu Val Lys Lys Pro Gly Ala
1 5 10 15

Ser Val Lys Val Ser Cys Thr Ala Ser Gly Tyr Thr Phe Thr His Tyr
20 25 30

Gly Met Asn Trp Val Arg Gln Ala Pro Gly Lys Gly Leu Glu Trp Met
35 40 45

Gly Arg Ile Asn Pro Asp Ser Gly Asp Thr Ile Tyr Ala Gln Lys Phe
50 55 60

Gln Asp Arg Phe Thr Phe Ser Leu Glu Thr Ser Ala Ser Thr Val Tyr
65 70 75 80

Met Glu Leu Thr Ser Leu Thr Ser Asp Asp Thr Ala Val Tyr Tyr Cys
85 90 95

Ala Arg Glu Arg Gly Asp Ala Met Asp Tyr Trp Gly Gln Gly Thr Leu
100 105 110

Val Thr Val Ser Ser
115

<210> SEQ ID NO 10
<211> LENGTH: 20
<212> TYPE: PRT
<213> ORGANISM: artificial linker
<220> FEATURE:
<223> OTHER INFORMATION: synthetic linker sequence

<400> SEQUENCE: 10

Gly Gly Gly Gly Ser Gly Gly Gly Gly Ser Gly Gly Gly Gly Ser Gly
1 5 10 15

Gly Gly Gly Ser
20

<210> SEQ ID NO 11
<211> LENGTH: 108
<212> TYPE: PRT
<213> ORGANISM: artificial
<220> FEATURE:
<223> OTHER INFORMATION: derivative of TB-B

<400> SEQUENCE: 11

Asp Ile Val Leu Thr Gln Ser Pro Ser Ser Leu Ser Ala Ser Val Gly
1 5 10 15

Asp Arg Val Thr Leu Thr Cys Thr Ala Ser Gln Ser Val Ser Asn Asp
20 25 30

Val Val Trp Tyr Gln Gln Arg Pro Gly Lys Ala Pro Lys Leu Leu Ile
35 40 45

Tyr Ser Ala Phe Asn Arg Tyr Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Val Ala Val Tyr Tyr Cys Gln Gln Asp Tyr Asn Ser Pro Arg
85 90 95

```
Thr Phe Gly Gln Gly Thr Lys Leu Glu Val Lys Arg
            100                 105


<210> SEQ ID NO 12
<211> LENGTH: 245
<212> TYPE: PRT
<213> ORGANISM: artificial
<220> FEATURE:
<223> OTHER INFORMATION: scFV , human-murine with artificial linker

<400> SEQUENCE: 12

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Ser Phe Thr His Tyr
145                 150                 155                 160

Gly Met Asn Trp Val Arg Gln Ala Pro Gly Gln Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Val Thr Leu Thr Arg Asp Thr Ser Ile Gly Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 13
<211> LENGTH: 245
<212> TYPE: PRT
<213> ORGANISM: artificial
<220> FEATURE:
<223> OTHER INFORMATION: scFv, human-murine with artificial linker

<400> SEQUENCE: 13

Asp Ile Val Leu Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Arg Leu Ile
        35                  40                  45
```

Tyr Ser Ala Phe Asn Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245

<210> SEQ ID NO 14
<211> LENGTH: 106
<212> TYPE: PRT
<213> ORGANISM: human

<400> SEQUENCE: 14

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 15
<211> LENGTH: 105
<212> TYPE: PRT
<213> ORGANISM: human

<400> SEQUENCE: 15

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Ser Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Thr Ser
            100                 105


<210> SEQ ID NO 16
<211> LENGTH: 108
<212> TYPE: PRT
<213> ORGANISM: murine

<400> SEQUENCE: 16

Asp Ile Val Met Thr Gln Thr Pro Lys Phe Leu Leu Val Ser Ala Gly
1               5                   10                  15

Asp Arg Val Thr Ile Thr Cys Thr Ala Ser Gln Ser Val Ser Asn Asp
            20                  25                  30

Val Val Trp Tyr Gln Gln Lys Pro Gly Gln Ser Pro Lys Met Leu Met
        35                  40                  45

Tyr Ser Ala Phe Asn Arg Tyr Thr Gly Val Pro Asp Arg Phe Thr Gly
    50                  55                  60

Arg Gly Tyr Gly Thr Asp Phe Thr Phe Thr Ile Ser Ser Val Gln Ala
65                  70                  75                  80

Glu Asp Leu Ala Val Tyr Phe Cys Gln Gln Asp Tyr Asn Ser Pro Arg
                85                  90                  95

Thr Phe Gly Gly Gly Thr Lys Leu Glu Ile Lys Arg
            100                 105


<210> SEQ ID NO 17
<211> LENGTH: 117
<212> TYPE: PRT
<213> ORGANISM: murine

<400> SEQUENCE: 17

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Glu His Phe Ala Phe Ser Leu Glu Thr Ser Ala Ser Thr Val Phe
65                  70                  75                  80

Leu Gln Ile Asn Asn Leu Lys Asn Glu Asp Thr Ala Thr Tyr Phe Cys
                85                  90                  95

Ala Arg Glu Arg Gly Asp Ala Met Asp Tyr Trp Gly Gln Gly Thr Ser
            100                 105                 110

Val Thr Val Ser Ser
        115
```

<210> SEQ ID NO 18
<211> LENGTH: 245
<212> TYPE: PRT
<213> ORGANISM: artificial
<220> FEATURE:
<223> OTHER INFORMATION: scFV, human-murine with artificial linker

<400> SEQUENCE: 18

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Gln Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245

<210> SEQ ID NO 19
<211> LENGTH: 245
<212> TYPE: PRT
<213> ORGANISM: artificial
<220> FEATURE:
<223> OTHER INFORMATION: scFv, human-murine with artificial linker

<400> SEQUENCE: 19

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro

```
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Val Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 20
<211> LENGTH: 245
<212> TYPE: PRT
<213> ORGANISM: artificial
<220> FEATURE:
<223> OTHER INFORMATION: scFv, human-murine with artificial linker

<400> SEQUENCE: 20

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190
```

```
Lys Asp Arg Phe Thr Leu Ser Arg Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 21
<211> LENGTH: 245
<212> TYPE: PRT
<213> ORGANISM: artificial
<220> FEATURE:
<223> OTHER INFORMATION: scFv, human-murine with artificial linker

<400> SEQUENCE: 21

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ile Gly Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 22
<211> LENGTH: 245
<212> TYPE: PRT
<213> ORGANISM: artificial
<220> FEATURE:
<223> OTHER INFORMATION: scFv, human-murine with artificial linker

<400> SEQUENCE: 22
```

```
Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Arg Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245
```

<210> SEQ ID NO 23
<211> LENGTH: 245
<212> TYPE: PRT
<213> ORGANISM: artificial
<220> FEATURE:
<223> OTHER INFORMATION: scFv, human-murine with artificial linker

<400> SEQUENCE: 23

```
Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110
```

```
Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 24
<211> LENGTH: 245
<212> TYPE: PRT
<213> ORGANISM: artificial
<220> FEATURE:
<223> OTHER INFORMATION: scFv, human-murine with artificial linker

<400> SEQUENCE: 24

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
```

225 230 235 240

Val Thr Val Ser Ser
245

<210> SEQ ID NO 25
<211> LENGTH: 117
<212> TYPE: PRT
<213> ORGANISM: artificial
<220> FEATURE:
<223> OTHER INFORMATION: derived from TB-A

<400> SEQUENCE: 25

Gln Val Gln Leu Val Gln Ser Gly Ala Glu Val Lys Lys Pro Gly Ala
1 5 10 15

Ser Val Lys Val Ser Cys Thr Ala Ser Gly Tyr Thr Phe Thr His Tyr
20 25 30

Gly Met Asn Trp Val Arg Gln Ala Pro Gly Lys Gly Leu Glu Trp Met
35 40 45

Gly Trp Ile Asn Thr Tyr Thr Gly Glu Pro Thr Tyr Ala Asp Lys Phe
50 55 60

Lys Gly Arg Phe Thr Phe Ser Leu Glu Thr Ser Ala Ser Thr Val Tyr
65 70 75 80

Met Glu Leu Thr Ser Leu Thr Ser Asp Asp Thr Ala Val Tyr Tyr Cys
85 90 95

Ala Arg Glu Arg Gly Asp Ala Met Asp Tyr Trp Gly Gln Gly Thr Leu
100 105 110

Val Thr Val Ser Ser
115

<210> SEQ ID NO 26
<211> LENGTH: 108
<212> TYPE: PRT
<213> ORGANISM: artificial
<220> FEATURE:
<223> OTHER INFORMATION: derived from TB-A

<400> SEQUENCE: 26

Asp Ile Val Met Thr Gln Ser Pro Ser Ser Leu Ser Ala Ser Val Gly
1 5 10 15

Asp Arg Val Thr Leu Thr Cys Thr Ala Ser Gln Ser Val Ser Asn Asp
20 25 30

Val Val Trp Tyr Gln Gln Arg Pro Gly Lys Ala Pro Lys Leu Leu Ile
35 40 45

Tyr Ser Ala Phe Asn Arg Tyr Thr Gly Val Pro Ser Arg Phe Ser Gly
50 55 60

Arg Gly Tyr Gly Thr Asp Phe Thr Leu Thr Ile Ser Ser Leu Gln Pro
65 70 75 80

Glu Asp Phe Ala Val Tyr Tyr Cys Gln Gln Asp Tyr Asn Ser Pro Arg
85 90 95

Thr Phe Gly Gln Gly Thr Lys Leu Glu Val Lys Arg
100 105

<210> SEQ ID NO 27
<211> LENGTH: 108
<212> TYPE: PRT
<213> ORGANISM: artificial
<220> FEATURE:
<223> OTHER INFORMATION: derived from TB-A

<400> SEQUENCE: 27

```
Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Ala Ala Val Tyr Tyr Cys Gln Gln Asp Tyr Asn Ser Pro Arg
                85                  90                  95

Thr Phe Gly Gln Gly Thr Lys Leu Glu Val Lys Arg
            100                 105


<210> SEQ ID NO 28
<211> LENGTH: 117
<212> TYPE: PRT
<213> ORGANISM: artificial
<220> FEATURE:
<223> OTHER INFORMATION: derived from TB-A

<400> SEQUENCE: 28

Gln Val Gln Leu Val Gln Ser Gly Ala Glu Val Lys Lys Pro Gly Ala
1               5                   10                  15

Ser Val Lys Val Ser Cys Thr Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Lys Asp Arg Phe Thr Leu Thr Leu Asp Thr Ser Ala Gly Thr Val Tyr
65                  70                  75                  80

Met Glu Leu Thr Ser Leu Thr Ser Asp Asp Thr Ala Val Tyr Tyr Cys
                85                  90                  95

Ala Arg Glu Arg Gly Asp Ala Met Asp Tyr Trp Gly Gln Gly Thr Leu
            100                 105                 110

Val Thr Val Ser Ser
        115


<210> SEQ ID NO 29
<211> LENGTH: 117
<212> TYPE: PRT
<213> ORGANISM: artificial
<220> FEATURE:
<223> OTHER INFORMATION: derived from TB-A

<400> SEQUENCE: 29

Gln Val Gln Leu Val Gln Ser Gly Ala Glu Val Lys Lys Pro Gly Ala
1               5                   10                  15

Ser Val Lys Val Ser Cys Thr Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Lys Asp Arg Phe Thr Leu Thr Leu Glu Thr Ser Ala Ser Thr Val Tyr
65                  70                  75                  80
```

```
Met Glu Leu Thr Ser Leu Thr Ser Asp Asp Thr Ala Val Tyr Tyr Cys
                85                  90                  95

Ala Arg Glu Arg Gly Asp Ala Met Asp Tyr Trp Gly Gln Gly Thr Leu
            100                 105                 110

Val Thr Val Ser Ser
        115


<210> SEQ ID NO 30
<211> LENGTH: 117
<212> TYPE: PRT
<213> ORGANISM: artificial
<220> FEATURE:
<223> OTHER INFORMATION: derived from TB-A

<400> SEQUENCE: 30

Gln Val Gln Leu Val Gln Ser Gly Ala Glu Asp Lys Lys Pro Gly Gly
1               5                   10                  15

Ser Val Lys Val Ser Cys Thr Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Lys Gly Arg Phe Thr Leu Thr Leu Asp Thr Ser Ala Gly Thr Val Tyr
65                  70                  75                  80

Met Glu Leu Thr Ser Leu Thr Ser Asp Asp Thr Ala Thr Tyr Tyr Cys
                85                  90                  95

Ala Arg Glu Arg Gly Asp Ala Met Asp Tyr Trp Gly Gln Gly Thr Ser
            100                 105                 110

Val Thr Val Ser Ser
        115


<210> SEQ ID NO 31
<211> LENGTH: 245
<212> TYPE: PRT
<213> ORGANISM: artificial
<220> FEATURE:
<223> OTHER INFORMATION: Derivative of TB-A

<400> SEQUENCE: 31

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140
```

```
Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Leu
                165                 170                 175

Gly Trp Ile Asn Thr Tyr Thr Gly Glu Pro Thr Tyr Ala Asp Lys Phe
            180                 185                 190

Lys Asp Arg Ile Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 32
<211> LENGTH: 245
<212> TYPE: PRT
<213> ORGANISM: artificial
<220> FEATURE:
<223> OTHER INFORMATION: Derivative of TB-A

<400> SEQUENCE: 32

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Glu Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ala Ser Thr Ala Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245
```

<210> SEQ ID NO 33
<211> LENGTH: 245
<212> TYPE: PRT
<213> ORGANISM: artificial
<220> FEATURE:
<223> OTHER INFORMATION: Derivative of TB-A

<400> SEQUENCE: 33

```
Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Arg Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Leu Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245
```

<210> SEQ ID NO 34
<211> LENGTH: 245
<212> TYPE: PRT
<213> ORGANISM: artificial
<220> FEATURE:
<223> OTHER INFORMATION: Derivative of TB-A

<400> SEQUENCE: 34

```
Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
```

```
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Arg Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Ile Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 35
<211> LENGTH: 245
<212> TYPE: PRT
<213> ORGANISM: artificial
<220> FEATURE:
<223> OTHER INFORMATION: Derivative of TB-A

<400> SEQUENCE: 35

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190
```

```
Lys Asp Arg Leu Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 36
<211> LENGTH: 245
<212> TYPE: PRT
<213> ORGANISM: artificial
<220> FEATURE:
<223> OTHER INFORMATION: Derivative of TB-A

<400> SEQUENCE: 36

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Ala Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 37
<211> LENGTH: 245
<212> TYPE: PRT
<213> ORGANISM: artificial
<220> FEATURE:
<223> OTHER INFORMATION: Derivative of TB-A

<400> SEQUENCE: 37
```

```
Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Val Thr Leu Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 38
<211> LENGTH: 245
<212> TYPE: PRT
<213> ORGANISM: artificial
<220> FEATURE:
<223> OTHER INFORMATION: Derivative of TB-A

<400> SEQUENCE: 38

Asp Ile Val Met Thr Gln Ser Pro Ser Ser Leu Ser Ala Ser Val Gly
1               5                   10                  15

Asp Arg Val Thr Leu Thr Cys Thr Ala Ser Gln Ser Val Ser Asn Asp
            20                  25                  30

Val Val Trp Tyr Gln Gln Arg Pro Gly Lys Ala Pro Lys Leu Leu Ile
        35                  40                  45

Tyr Ser Ala Phe Asn Arg Tyr Thr Gly Val Pro Ser Arg Phe Ser Gly
    50                  55                  60

Arg Gly Tyr Gly Thr Asp Phe Thr Leu Thr Ile Ser Ser Leu Gln Pro
65                  70                  75                  80

Glu Asp Val Ala Val Tyr Tyr Cys Gln Gln Asp Tyr Asn Ser Pro Arg
                85                  90                  95

Thr Phe Gly Gln Gly Thr Lys Leu Glu Val Lys Arg Gly Gly Gly Gly
            100                 105                 110
```

-continued

Ser Gly Gly Gly Gly Ser Gly Gly Gly Gly Ser Gly Gly Gly Gly Ser
115 120 125

Gln Val Gln Leu Val Gln Ser Gly Ala Glu Val Lys Lys Pro Gly Ala
130 135 140

Ser Val Lys Val Ser Cys Thr Ala Ser Gly Tyr Thr Phe Thr His Tyr
145 150 155 160

Gly Met Asn Trp Val Arg Gln Ala Pro Gly Lys Gly Leu Glu Trp Met
165 170 175

Gly Trp Ile Asn Thr Tyr Thr Gly Glu Pro Thr Tyr Ala Asp Lys Phe
180 185 190

Lys Asp Arg Phe Thr Leu Ser Leu Glu Thr Ser Ala Ser Thr Val Tyr
195 200 205

Met Glu Leu Thr Ser Leu Thr Ser Asp Asp Thr Ala Val Tyr Tyr Cys
210 215 220

Ala Arg Glu Arg Gly Asp Ala Met Asp Tyr Trp Gly Gln Gly Thr Leu
225 230 235 240

Val Thr Val Ser Ser
245

<210> SEQ ID NO 39
<211> LENGTH: 20
<212> TYPE: PRT
<213> ORGANISM: artificial
<220> FEATURE:
<223> OTHER INFORMATION: synthetic linker

<400> SEQUENCE: 39

Gly Arg Gly Gly Ser Gly Gly Gly Gly Ser Gly Gly Gly Gly Ser Gly
1 5 10 15

Gly Gly Gly Ser
20

<210> SEQ ID NO 40
<211> LENGTH: 245
<212> TYPE: PRT
<213> ORGANISM: artificial
<220> FEATURE:
<223> OTHER INFORMATION: TB-A scFv antibody

<400> SEQUENCE: 40

Asp Ile Val Met Thr Gln Ser Pro Ser Ser Leu Ser Ala Ser Val Gly
1 5 10 15

Asp Arg Val Thr Leu Thr Cys Thr Ala Ser Gln Ser Val Ser Asn Asp
20 25 30

Val Val Trp Tyr Gln Gln Arg Pro Gly Lys Ala Pro Lys Leu Leu Ile
35 40 45

Tyr Ser Ala Phe Asn Arg Tyr Thr Gly Val Pro Ser Arg Phe Ser Gly
50 55 60

Arg Gly Tyr Gly Thr Asp Phe Thr Leu Thr Ile Ser Ser Leu Gln Pro
65 70 75 80

Glu Asp Val Ala Val Tyr Tyr Cys Gln Gln Asp Tyr Asn Ser Pro Arg
85 90 95

Thr Phe Gly Gln Gly Thr Lys Leu Glu Val Lys Arg Gly Gly Gly Gly
100 105 110

Ser Gly Gly Gly Gly Ser Gly Gly Gly Gly Ser Gly Gly Gly Gly Ser
115 120 125

Gln Val Gln Leu Val Gln Ser Gly Ala Glu Val Lys Lys Pro Gly Ala
130 135 140

-continued

```
Ser Val Lys Val Ser Cys Thr Ala Ser Gly Tyr Thr Phe Thr His Tyr
145                 150                 155                 160

Gly Met Asn Trp Val Arg Gln Ala Pro Gly Lys Gly Leu Glu Trp Met
                165                 170                 175

Gly Trp Ile Asn Thr Tyr Thr Gly Glu Pro Thr Tyr Ala Asp Lys Phe
            180                 185                 190

Lys Asp Arg Phe Thr Phe Ser Leu Glu Thr Ser Ala Ser Thr Val Tyr
        195                 200                 205

Met Glu Leu Thr Ser Leu Thr Ser Asp Asp Thr Ala Val Tyr Tyr Cys
    210                 215                 220

Ala Arg Glu Arg Gly Asp Ala Met Asp Tyr Trp Gly Gln Gly Thr Leu
225                 230                 235                 240

Val Thr Val Ser Ser
                245


<210> SEQ ID NO 41
<211> LENGTH: 5
<212> TYPE: PRT
<213> ORGANISM: Artificial
<220> FEATURE:
<223> OTHER INFORMATION: synthetic peptide

<400> SEQUENCE: 41

Gly Gly Gly Gly Ser
1               5
```